United States Patent
Zhang et al.

(10) Patent No.: US 8,836,535 B2
(45) Date of Patent: Sep. 16, 2014

(54) MOBILE NETWORK TERMINAL DEVICE AND METHOD FOR MONITORING ELECTROPHYSIOLOGICAL DATA AND PATHOLOGICAL IMAGE

(75) Inventors: Jinjing Zhang, Jinan (CN); Yonggang Zhao, Jinan (CN); Haiqing Gao, Jinan (CN); Yujie Zhou, Jinan (CN); Shaowen Liu, Jinan (CN); Xiaohong Zhu, Jinan (CN)

(73) Assignee: Jinjing Zhang, Jinan (CN)

( * ) Notice: Subject to any disclaimer, the term of this patent is extended or adjusted under 35 U.S.C. 154(b) by 701 days.

(21) Appl. No.: 12/998,809

(22) PCT Filed: Apr. 21, 2009

(86) PCT No.: PCT/CN2009/000421
§ 371 (c)(1),
(2), (4) Date: Jul. 14, 2011

(87) PCT Pub. No.: WO2010/063158
PCT Pub. Date: Jun. 10, 2010

(65) Prior Publication Data
US 2011/0273309 A1 Nov. 10, 2011

(30) Foreign Application Priority Data
Dec. 5, 2008 (CN) .......................... 2008 1 0239037

(51) Int. Cl.
*G08C 19/22* (2006.01)
(52) U.S. Cl.
USPC .............. 340/870.07; 340/573.1; 340/286.07; 340/539.12; 379/38; 455/404.2; 600/301

(58) Field of Classification Search
USPC ................ 340/870.07, 870.09, 573.1, 573.4, 340/286.07, 539.1, 539.12, 539.11, 3.1, 340/5.61; 379/37, 38; 455/404.1, 404.2; 607/60; 600/300, 301, 481
See application file for complete search history.

(56) References Cited

U.S. PATENT DOCUMENTS

| | | | | |
|---|---|---|---|---|
| 7,330,122 | B2* | 2/2008 | Derrick et al. | 340/573.1 |
| 7,515,044 | B2* | 4/2009 | Welch et al. | 340/539.12 |
| 7,978,062 | B2* | 7/2011 | LaLonde et al. | 340/539.11 |

* cited by examiner

*Primary Examiner* — Anh V La
(74) *Attorney, Agent, or Firm* — CBM Patent Consulting, LLC

(57) ABSTRACT

A mobile network terminal device and method for monitoring the electrophysiological data and a pathological image are provided, including: a baseband processor module, an electrophysiological data collection module, a keyboard module, a graphics and image display module, an image and picture sensor, a voice communication module, an external data memory card, an external data memory, a Bluetooth module, a USB interface module, a GPS receiver module, an application module set and run in the operation system of the baseband processor; an electrophysiological data remote mobile monitoring, a heart pacemaker remote mobile monitoring, a remote consultation appointment, a pathological image remote mobile monitoring, a data exchange, a medical advisory VoIP communication and a network emergency call being performed by the mobile network terminal device under the control of the application module.

25 Claims, 15 Drawing Sheets

MOBILE NETWORK TERMINAL DEVICE AND METHOD FOR MONITORING ELECTROPHYSIOLOGICAL DATA AND PATHOLOGICAL IMAGE

TECHNICAL FIELD OF THE INVENTION

The present invention relates to a medical remote monitoring technology, more particularly, to a device for remotely monitoring electrophysiological data and a pathological image and a method thereof.

BACKGROUND OF THE INVENTION

In recent years, with the development of the mobile network technology, there appear cardiogram remote monitoring devices using a digital cell phone and a digital cell phone module, which apply the mobile network high speed wireless IP technology to collect and monitor the heart electrophysiological data of the patient population distributed over the society, and remotely send the data to a target hospital for analysis and diagnosis. This remote monitoring technology can treat patients in time, can reduce the mortality due to the cardiovascular disease, and becomes an important development content in the medical field for the mobile network technology.

In prior art, the digital cell phone or a baseband processor of the digital cell phone is usually coupled to a traditional cardiogram guardianship recorder through two ways, a physical connection or a short distance wireless radio frequency (RF) connection. FIG. 1 is a diagram of a discrete heart electrophysiological data remote mobile monitoring system of prior art, as in the U.S. Pat. No. 6,801,137, and the Chinese patent application No. 03116539.7. A cardiogram guardianship recorder 12 is coupled with a dedicated digital cell phone 10, and the cardiogram guardianship recorder 12 and the dedicated digital cell phone 10 are wirelessly connected to each other through a Bluetooth module. The cardiogram guardianship recorder 12 is a cardiogram signal collection system controlled by a microprocessor MCU, in which includes at least a cardiogram signal collection circuit, an Analog to digital (AD) convertor, a program memory, a data buffer memory, a system clock, a Bluetooth, a work power supply, an application software, and so on. The cardiogram guardianship recorder 12 is responsible for collecting a cardiogram analog signal data, obtaining a digital signal data via an analog to digital conversion, then buffering and storing the converted digital signal data, and transmitting the digital signal data to a Bluetooth module 11 of the dedicated digital cell phone 10 through a Bluetooth module 13. The dedicated digital cell phone 10 is an integral digital cell phone system, including an operation system and an application program. The dedicated digital cell phone 10 is responsible for receiving the data transmitted from the cardiogram guardianship recorder 12, and then processing and storing the received data. When a user requires sending data, a mobile network is registered by operating the dedicated digital cell phone. Then the monitoring data is transmitted to a target server, and an analysis process result is obtained.

The disadvantage of the above prior technology is that the monitoring data has to be received and processed continuously by means of the dedicated digital cell phone, and when the patient turns off the dedicated digital cell phone in an environment such as an air plane flight, a heart monitoring is terminated at the same time. As illustrated in FIG. 1, although part of hardware and functions of the cardiogram guardianship recorder 12 is simplified, and the powerful hardware and software functions of the dedicated digital cell phone 10 are applied more, it can just works continuously for several hours to obtain some segmented cardiogram monitoring data because of the massive power consumption of the Bluetooth transmission/reception and the operation of the digital cell phone. Such segmented cardiogram monitoring data does not have significant effect and advantage for most patient users who require a long time monitoring. Meanwhile, it can not provide 24 hours continuous monitoring data required by doctors in the hospital when they review and analyze the cardiogram data. During the usage, the patient user has to carry one dedicated digital cell phone additionally, charge or replace a battery frequently, which is inconvenient to the daily life of the user. Meanwhile, the manufacture cost of the dedicated digital cell phone is expensive, and the patient user has to afford a higher application cost.

FIG. 2 illustrates a diagram of an integrated heart electrophysiological data remote mobile monitoring system of the prior art, as in the Chinese patent applications No. 200520054381.8, 200510115114.1 and 200610030198.3. A cardiogram guardianship recorder 20 is coupled to a baseband processor 21, and the cardiogram guardianship recorder 20 and the baseband processor 21 are connected to each other through their asynchronous series data communication ports UART. The cardiogram guardianship recorder 20 includes at least a microprocessor MCU module, a cardiogram data collection module, a liquid crystal module, a keyboard module, a USB module, an external data storage card, an external data memory, a system clock, a work power supply manager, an internal multiple analog to digital (AD) convertor, an asynchronous series communication port UART, and an application program, etc., for the collection process and storage of the cardiogram data. The baseband processor 21 is a baseband processor of a general GPRS or CDMA digital cell phone, in which there is a mobile voice communication and wireless data communication module of which the cores are a microprocessor MCU and a digital signal processor, and in which there are at least a coprocessor, a system and periphery bus, a periphery bus interface, an internal data memory, a Direct Access Memory DMA, a buffer memory, a work power supply manager, a baseband unit, a frequency control unit, a system clock, a real time clock, a timer, and a periphery instrument and interface. The periphery instrument and the interface thereof include: a multiple analog to digital (AD) convertor unit, a keyboard control unit, a liquid crystal control unit, an audio process unit, an external data storage card control unit, an external data memory Flash control unit, an asynchronous series communication port UART unit, a USB controller unit, a SIM card control unit, a JTAG test unit, a radio frequency antenna, and an operation system and TCP/IP protocol, etc. As illustrated in FIG. 2, most of the function units and the periphery instruments of the baseband processor are in an idle status. When sending the monitoring data, the cardiogram guardianship recorder 20 controls the baseband processor 21 to start-up operation through the asynchronous series data communication port UART, registers with the mobile network, and makes a network data information exchange.

As the design method in FIG. 2, the primary cause is that the baseband processor is a mobile voice communication and wireless data communication chip, only the asynchronous series communication ports UART are opened, the external application and the base support of other application fields are not considered by manufacturers, and changing the base control program of the baseband processor is a very difficult work in technology. Therefore, it has to employ the cardiogram guardianship recorder 20 and the baseband processor 21 which are connected to each other through the asynchronous series communication port UART and integrated into a physical entity. In addition, there is a similar technology applying a low cost baseband processor module. However, due to the lack of TCP/IP protocol, a further expensive network processor hardware unit, for example, the IP 2000, is required between the cardiogram guardianship recorder 20 and the baseband processor module 21. The cardiogram guardianship recorder 20 may control the baseband processor 21 to be in a "sleep" status, which reduces the power consumption of the device, so as to be capable of continuously monitoring and recording cardiogram data for a long time. Moreover, the integrated structure is convenient for the user to carry and use. However, the disadvantage of such technology is that the structure of the hardware system is complicated and redundant; most of the hardware and functions, such as the multiple analog to digital (AD) convertor, within the baseband processor are idle and wasted, only the data communication function of the baseband processor gets used. Such superimposition of the low level causes not only the waste of resource and the reduction of reliability, but also a higher level of the operation power consumption. Accordingly, the whole machine requires a larger hardware space and a higher manufacture cost.

SUMMARY OF THE INVENTION

The object of the present invention is to solve the problem existed in the prior art, provide a mobile network terminal device for monitoring body electrophysiological data and a pathological image monitoring and a method thereof, which are low in the manufacture cost, reliable and convenient to use.

The present invention provides a mobile network terminal device for monitoring electrophysiological data and a pathological image, characterized in that, comprises a baseband processor module, an electrophysiological data collection module, a keyboard module, a graphic and image display module, an image and picture sensor, a voice communication module, an external data storage card, an external data memory, a Bluetooth module, a USB interface module, a GPS receiver module, an application program module operated in an operation system of the baseband processor module. The operation system is further embedded a TCP/IP protocol, a Bluetooth protocol, a USB protocol, a WAP browser, an instant communication protocol, a VoIP protocol, a multimedia software, and a primary language text font. Under the control of the application program module, the mobile network terminal device sets user information data, a function status, and a work mode; makes a remote mobile monitoring of the electrophysiological data, a remote mobile monitoring of a electrophysiological data in special occasions, a remote mobile monitoring of a heart pacemaker, a reservation remote consultation, a remote mobile monitoring of a pathological image, a Bluetooth short distance data/information exchange, a USB large volume data/information exchange, a medical consultation VoIP voice communication, and a network emergency recourse; and views a medical material electronic text, an intelligence recovery game, and a video clip playing in a multimedia work status.

The features of the present invention lie in the baseband processor module of the mobile network terminal device collects and processes an electrophysiological analog data signal, including pathological image/picture video data; establishes a data connection to a remote server over the mobile network according to the user information data set by the mobile network terminal device; makes a network data/information exchange; and implements various function at the same time. The baseband processor module includes at least the operation system, a microprocessor unit (MCU), a digital signal processor unit, a coprocessor unit, a system bus, a periphery bus, a bridge unit, an interface for the periphery bus, a data memory unit, a direct access memory unit, a buffer memory unit, a power supply management unit, a baseband unit, a frequency control unit, a system clock unit, a real time clock unit, a timer GPT unit, and a periphery instrument and an interface thereof. The periphery instrument and the interface thereof include at least a multiple analog to digital (AD) convertor unit, a keyboard control unit, a graphic and image display control unit, an image/picture collection process unit, an audio process unit, an external data storage card control unit, an external data memory control unit, an asynchronous series communication port UART unit, a USB controller unit, a JTAG test unit, a SIM card control unit, and a radio frequency antenna.

The features of the present invention lie in the microprocessor unit (MCU) of the baseband processor module controls the operation of each function unit and periphery instrument; the system clock unit provides the system with a task schedule reference; the real time clock unit provides a data collection timer GPT with a clock source; the power supply management unit provides each function unit and periphery instrument with a power supply; The GPTn in the timer GPT unit generates a preset interrupt frequency, and controls a analog to digital conversion sampling frequency; the buffer memory unit buffers various data; The SIM card control unit is connected to a client identity recognition SIM card so as to provide the mobile network with identity recognition data of a local host; the baseband unit and the frequency control unit are connected with the radio frequency antenna, so as to control the modulation and demodulation of the signal, and the signal conversion between an external radio frequency signal and a signal of the baseband unit; the multiple analog to digital (AD) convertor unit is connected to the electrophysiological data collection module, so as to convert the electrophysiological analog signal to a digital signal; the keyboard control unit is connected to the keyboard module, so as to issue various control instructions of the mobile network terminal device, and input and/or set user information data; the graphic and image display control unit is connected to the graphic and image display module, so as to display a human machine interaction interface, a selection list, and a medical material electronic text viewing pages in the multimedia work status, and so on; the image/picture collection process unit is connected to the image and picture sensor, so as to collect the pathological image/picture video data of the user; the audio process unit is connected to the voice communication module, so as to enable the VoIP voice communication of the mobile network terminal device, and a process of a voice broadcasting of the doctor's advice, the doctor's leave word, etc.; the external data storage card control unit is connected to the external data storage card, so as to encode and store respective electrophysiological monitoring data, pathological image video data, and external forward data of the mobile network terminal device by partitions; the external data memory control unit is connected to the external data memory, so as to store an application program of the mobile network terminal device, including a user information file and a configuration file, user setting information data, two dimensional recognition data, and medical evidence data, etc.; a UART1 in an asynchronous series communication port UART unit is connected to the Bluetooth module, so as to enable a short distance data/information exchange between the mobile network terminal device and an external device, and a UART2 is connected to the GPS receiver module, so as to enable a satellite positioning of the mobile network terminal device; the USB controller unit is connected to the USB interface module, so as to enable a large volume data/information exchange between the mobile network terminal device and a computer device.

The features of the present invention lie in that the electrophysiological data collection module of the mobile network terminal device includes at least multiple analog signal channels, which can be connected to multiple cardiogram sensors so as to synchronously collect multiple cardiogram analog signal data including pacemaker pulse signal data, or can be connected to a cardiogram, a blood pressure, a breath sensors at the same time so as to synchronously collect analog signal data of the cardiogram, the blood pressure, and the breath; the output end of each analog signal channel is connected to the input end of each channel of the multiple AD convertor unit of the baseband processor module, so as to convert the analog signal to the digital signal, and send the digital signal to the baseband processor module for a further process.

The features of the present invention lie in that the mobile network terminal device sets an analog to digital conversion sampling rate under the control of the application program module. The application program module controls an interrupt frequency of the timer unit GPTn of the baseband processor module to be an integer power of 2 at the time of data collection according to the work mode flag, and controls an interrupt callback function to be a sampling function or a frequency-division sampling function. The timer unit GPTn independently and automatically generates the preset interrupt frequency when the interrupt frequency is the integer power of 2, and controls the analog signal sampling frequency or the frequency-division sampling frequency of each channel of the multiple analog to digital (AD) convertor unit, and the range of the sampling frequency is set between 128 Hz and 16,384 Hz. The sampling function or frequency-division sampling function reads each channel data of the multiple analog to digital (AD) convertor unit according to an interruption flag of the timer unit GPTn, and sends the data to the buffer memory unit of the baseband processor module for storage. The sampling function or frequency-division sampling function sends a record storage flag regularly, and the microprocessor unit (MCU) of the baseband processor module performs a storage command, reads the data stored in the buffer memory unit, and sends the data to a preset area of the external data storage card for storage.

The features of the present invention lies in that the external data memory of the mobile network terminal device is used to store user information data input and/or set by the keyboard module. The user information data includes, but is not limited to, an access point domain name APN, a target server fixed IP address, a user name and password, a SMS number, a MMS address, VoIP access information, a default target address list, a user identity, a dwelling location, a blood type, a society medical guardianship card number, a medical record summary containing a user disease diagnosis, and recourse text information. The user information data is used to a wireless access and a data/information exchange for a network level, and is used to provide an identity authentication and a brief disease history in the data exchange, and is also used to establish a VoIP voice communication channel between the mobile network terminal device and the callee at the target end, so as to make voice medical consultation and send a recourse text of "need help" over the mobile network.

The features of the present invention lies in that the external data storage card of the mobile network terminal device is encoded so as to be divided into a continuous electrophysiological data storage area, an abnormal electrophysiological data storage area, a pathological image video data storage area, an external forward data storage area, a position information data storage area, a multimedia data storage area under the control of the application program module. These storage areas are respectively used to store 24 hours continuous monitoring electrophysiological data, abnormal electrophysiological frame data, pathological image video data, external forward data, position information data, multimedia data, various analysis diagnosis parameter information, statistic information, and time information of the mobile network terminal device. When the mobile network terminal device makes a data/information exchange at the network level, it reads data from the preset area of the external data storage card, packetizes the data. The packetized data further includes the data of the local host user medical record summary, the society medical insurance card number, and the position information.

The present invention provides a method for monitoring electrophysiological data and a pathological image, the method comprises operating the application program module in an operation system, controlling and/or setting a work mode of the mobile network terminal device, the work mode includes an electrophysiological data monitoring mode, an electrophysiological data special monitoring mode, an heart pacemaker monitoring mode, a reservation remote consultation mode, a pathological image monitoring mode, a short distance data communication mode, a VoIP voice communication mode, and a network emergency recourse mode, in particularly, the method includes the steps of:

[1] the work mode of the mobile network terminal device is selected and/or set according to instructions generated from operating a keyboard by a user, and a work mode recognition flag is sent;

[2] when the electrophysiological data monitoring mode is selected in step [1], according to the work mode recognition flag, the mobile network terminal device sets an interrupt frequency of a timer unit GPTn of the baseband processor module to be an integer power of 2, sets an interrupt callback function to be a sampling function, and sets a sampling frequency to be at least 128 Hz by the application program module;

[3] in step [2], the mobile network terminal device reads an access point domain name APN and a target server IP address simultaneously, registers with the mobile network, establishes a data connection to the target server, and sends a local host user flag and a service category request flag;

[4] according to a response flag replied from the target server, the mobile network terminal device controls a microprocessor unit (MCU) of the baseband processor module to enter a sleep state, and keeps an online network connection by the application program module;

[5] data of each channel of a multiple analog to digital (AD) convertor unit of the baseband processor module is read by the sampling function according to the preset sampling frequency, and the electrophysiological data is sent to and stored in a buffer memory unit of the baseband processor module;

[6] a record storage flag is regularly sent by the sampling function, and the microprocessor unit (MCU) of the baseband processor module performs a storage command, reads data from the buffer memory unit, and then sends the data to and stores the data in a preset area of a external data storage card;

[7] the electrophysiological data is analyzed by the application program module, if the electrophysiological data exceeds an alert threshold, an alarm category flag will be set, and an audio alert and/or a vibration alert, a light alert, and a text alert will be sent;

[8] according to the alarm category flag, the mobile network terminal device reads event data stored in the external data memory card, packetizes the data, and makes a data/information exchange over the network under the control of the application program module;

[9] the target server sends a command online, and the mobile network terminal device performs instructions of the target server according to the target server command flag.

Meanwhile, the method further includes the steps of:

[10] when the electrophysiological data special monitoring mode is selected in step [1], according to the work mode recognition flag, the mobile network terminal device turns off power supplies of a voice module and a radio frequency unit of the baseband processor module under the control of the application program module;

[11] in step [10], the mobile network terminal device sets the interrupt frequency of the timer unit GPTn of the baseband processor module to be an integer power of 2, sets the interrupt callback function to be the sampling function, and sets the sampling frequency to be at least 128 Hz;

[12] data of each channel of the multiple analog to digital (AD) convertor unit of the baseband processor module is read by the sampling function according to the preset sampling frequency, and the electrophysiological data is sent to and stored in the buffer memory unit;

[13] the record storage flag is regularly sent by the sampling function, and the microprocessor unit (MCU) of the baseband processor module performs the storage command, reads data from the buffer memory unit; and then sends the data to and stores the data in a preset area of the external data storage card;

[14] the electrophysiological data is analyzed by the application program module, if the electrophysiological data exceeds the alert threshold, the alarm category flag will be set, the vibration alert and/or the light alert, and the text alert will be sent so as to prompt the user to launch a network data communication function by operating the keyboard;

[15] according to instructions from the user keyboard, the mobile network terminal device activates the radio frequency antenna unit of the baseband processor module, reads the access point domain name APN and the target server IP address, registers with the mobile network, establishes the data connection to the target server, and sends the local host user flag and the service category request flag;

[16] according to the response flag replied from the target server, the mobile network terminal device reads event data stored in the external data memory card, packetizes the data, and makes a data/information exchange over the network under the control of the application program module.

Meanwhile, the method further includes the steps of:

[17] when the heart pacemaker monitoring mode is selected in step [1], according to the work mode recognition flag, the mobile network terminal device turns off the power supply of the radio frequency antenna unit of the baseband processor module under the control of the application program module;

[18] in step [17], the mobile network terminal device raises the interrupt frequency of the timer unit GPTn of the baseband processor module simultaneously, sets the interrupt frequency to be the integer power of 2, sets the interrupt callback function to be a frequency-division sampling function, sets the sampling frequency of the pacemaker pulse channel to be at least 2,048 Hz, and sets the sampling frequency of the cardiogram data channel to be at least 128 Hz;

[19] data of each channel of the multiple analog to digital (AD) convertor unit of the baseband processor module is read by the frequency-division sampling function according to the preset frequency-division sampling frequency, the pacemaker pulse data is compressed, and then sent to and stored in the buffer memory unit;

[20] the record storage flag is regularly sent by the frequency-division sampling function, and the microprocessor unit (MCU) of the baseband processor module performs the storage command, reads data from the buffer memory unit, and then sends the data to and stores the data in a preset area of the external data storage card;

[21] the pacemaker pulse data is analyzed by the application program module, if the pacemaker pulse data exceeds the alert threshold, the alarm category flag will be set, the audio alert and/or the vibration alert, the light alert, and the text alert will be sent so as to prompt the user to launch a network data communication function by operating the keyboard;

[22] according to instructions from the user keyboard, the mobile network terminal device activates the radio frequency antenna unit of the baseband processor module, reads the access point domain name APN and the target server IP address, registers with the mobile network, establishes the data connection to the target server, and sends the local host user flag and the service category request flag;

[23] according to the response flag replied from the target server, the mobile network terminal device reads event data stored in the external data memory card, packetizes the data, and makes a data/information exchange over the network under the control of the application program module.

Meanwhile, the method further includes the steps of:

[24] when the reservation remote consultation mode is selected in step [1], according to the work mode recognition flag, the mobile network terminal device sets wake up time T of a real time clock unit of the baseband processor module;

[25] when the preset time T of the real time clock unit elapses, an activation signal flag will be sent;

[26] according to the activation signal flag, the mobile network terminal device reads the access point domain name APN and the target server IP address, registers with the mobile network, establishes the data connection to the target server, and sends the local host user flag and the service category request flag;

[27] according to the response flag replied from the target server, the mobile network terminal device reads data stored in the external data memory card, packetizes the data, and makes a data/information exchange over the network under the control of the application program module.

Meanwhile, the method further includes the steps of:

[28] when the pathological image monitoring mode is selected in step [1], according to the work mode recognition flag, the mobile network terminal device sets a pathological image monitoring time length T, and activates an image and picture sensor;

[29] the image and picture sensor focuses automatically, takes pathological image video data of the user, and then sends the data to and stores the data in a preset area of the external data storage card;

[30] when the pathological image monitoring preset time T elapses, the mobile network terminal device goes into a wait-to-send status;

[31] according to sending instructions issued from the user keyboard, the mobile network terminal device reads the access point domain name APN and the target server IP address, registers with the mobile network, establishes the data connection to the target server, and sends the local host user flag and the service category request flag;

[32] according to the response flag replied from the target server, the mobile network terminal device reads video data stored in the external data memory card, compresses a data packet, and makes a data/information exchange over the network under the control of the application program module.

Meanwhile, the method further includes the steps of:

[33] when the short distance data communication mode is selected in step [1], according to the work mode recognition flag, the mobile network terminal device activates a Bluetooth module to send a paging signal to an external device;

[34] according to a Bluetooth response flag "device access code (DAC)" of the external device, the Bluetooth module of the mobile network terminal device sends a FH synchronization packet, exchanges real time clock and flag information, and establishes a data channel connection;

[35] the mobile network terminal device reads data stored in the external data memory card under the control of the application program module, and makes a short distance data/information exchange;

[36] the Bluetooth module of the mobile network terminal device receives the data/information sent from the external device, sends the data/information to and stores the data/information in a preset area of the external data storage card under the control of the application program module;

[37] according to forwarding instructions issued from the user keyboard, the mobile network terminal device reads the access point domain name APN and the target server IP address, registers with the mobile network, establishes the data connection to the target server, and sends the local host user flag and the service category request flag;

[38] according to the response flag replied from the target server, the mobile network terminal device reads data stored in the external data memory card, packetizes the data, and forwards the data of the external device under the control of the application program module.

Meanwhile, the method further includes the steps of:

[39] when the VoIP voice communication mode is selected in step [1], according to the work mode recognition flag, the mobile network terminal device activates a voice module, and registers with the mobile network simultaneously;

[40] the mobile network terminal device calls a VoIP voice communication protocol by the application program module, reads VoIP access information and a default target address stored in the external data memory, and initiates a request for establishing a call;

[41] a callee at the target end makes a response to the request, and the mobile network terminal device and the callee at the target end make voice medical consultation or voice communication.

Meanwhile, the method further includes the steps of:

[42] when the network emergency recourse mode is selected in step [1], according to the work mode recognition flag, the mobile network terminal device sets the alarm category flag by the application program module, and sends the audio alert and/or the vibration alert and the light alert;

[43] the mobile network terminal device reads the access point domain name APN and the target server IP address stored in the external data memory, registers with the mobile network, establishes the data connection to the target server, and sends the local host user flag, a request flag "I need help", and position information data;

[44] according to the response flag replied from the target server, the mobile network terminal device quits the network emergency recourse work mode.

As compared with the prior art, the advantage of the present invention is that: the present invention overcomes the disadvantage of a complex system structure, a redundant hardware, a poor reliability, and a large power consumption in the prior art, simplifies the complex electrophysiological remote mobile monitoring device to be a single hardware system, and extends the application range of the baseband processor to the clinic physic data process filed, which improves the efficiency and the reliability, reduces the power consumption, decreases the space occupied by the hardware, lowers the manufacture cost, and has a broad application prospect.

The present invention extends the technological connotation of the electrophysiological remote monitoring effectively, achieves the functions of the electrophysiological data remote mobile monitoring, the pacemaker data remote mobile monitoring, the pathological image remote mobile monitoring, and the electrophysiological data remote mobile monitoring in special occasions, the short distance data communication, the medical consultation VoIP voice communication, the network emergency recourse, the multimedia medical materials electronic text viewing, and so on. In addition, the present invention has the features of a convenient operation, a small volume, a light weight, and a low cost, and can be a medical information tool for the user individual.

For a further explanation on the principle and characteristic of the present invention, the detailed illustration of the present invention will be made in connection with the drawings and the specific embodiments as follows.

DETAILED DESCRIPTION OF THE PREFERRED EMBODIMENTS

The specific embodiment of the present invention will be described in detail in connection with the drawings in the following.

In accordance with one embodiment of the present invention, taking a MT 6225 GPRS standard baseband processor module based on Nucleus operation system as an example, the mobile network terminal device of the present invention and the method thereof will be described. However, those skilled in this art should understand that the application of the present invention is not limited to the GPRS standard baseband processor module and the Nucleus operation system. In fact, other baseband processor modules and other operation systems (including, but being not limited to, Windows mobile, Android, Linux, Palm OS, Symbian, OSE, Nucleus, and Hopen, etc.) can also be applied to the present invention.

Figure 1:
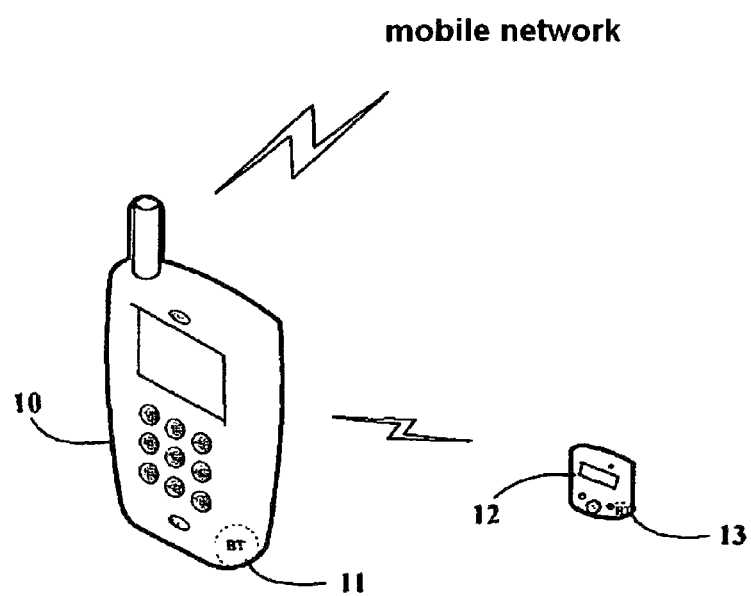
FIG. 1 is a diagram of the discrete cardiogram remote mobile monitoring instruments of the prior art, which are wirelessly connected by Bluetooth.
Figure 2:
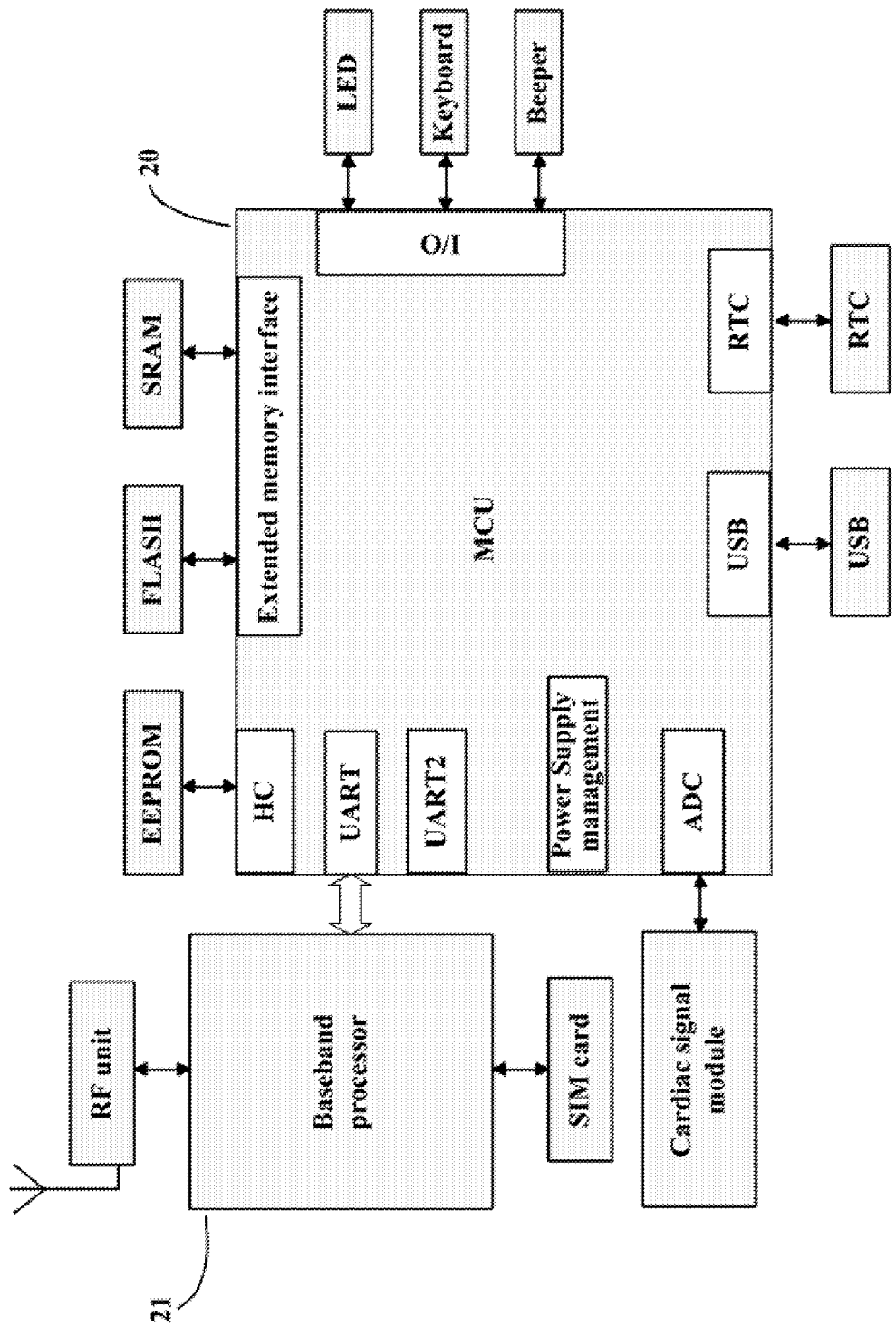
FIG. 2 is a principle block diagram of the integrated cardiogram remote mobile monitoring instrument of the prior art.
Figure 3:
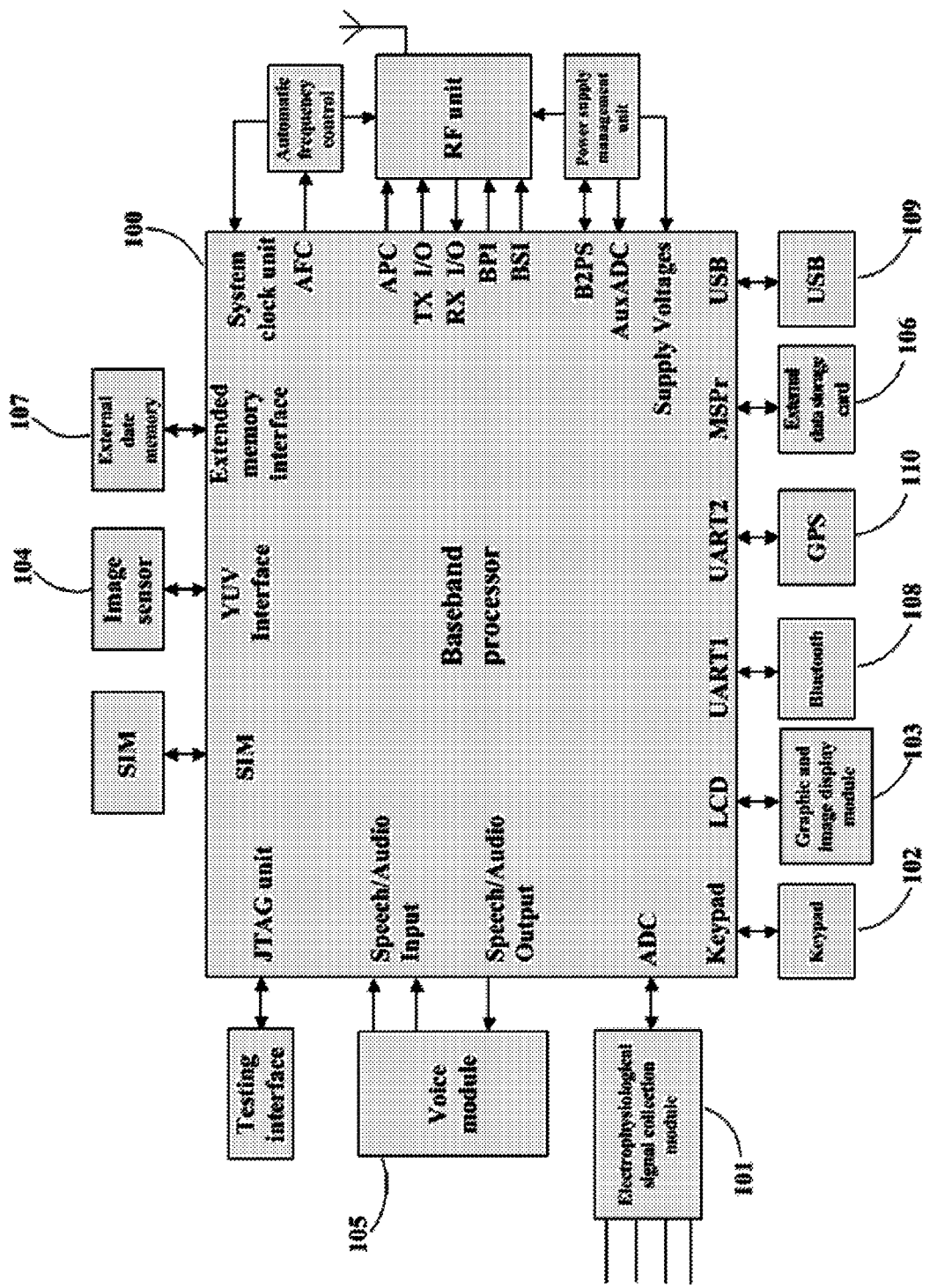
FIG. 3 is a principle block diagram of a mobile network terminal device for monitoring electrophysiological data and a pathological image according to one embodiment of the present invention.

FIG. 3 is a principle block diagram of a mobile network terminal device for monitoring electrophysiological data and a pathological image according to one embodiment of the present invention. The mobile network terminal device includes a GPRS baseband processor module 100, an electrophysiological signal collection module 101, a keyboard module 102, a graphic and image display module 103, an image and picture sensor 104, a voice module 105, an external data storage card 106, an external data memory 107, a Bluetooth module 108, a USB module 109, a GPS receiver module 110, and an application program module 200 set to operate under the Nucleus operation system in the GPRS baseband processor module 100. Moreover, the Nucleus operation system is further embedded with a TCP/IP protocol stack, a WAP browser, a Bluetooth protocol, a USB protocol, an instant message protocol, a VoIP voice communication protocol, a multimedia software, a general language text font, etc. Under the control of the application program, the mobile network terminal device selects and/or sets a user information data, a function status, a work mode; makes electrophysiological data remote mobile monitoring, electrophysiological data special occasion remote mobile monitoring, a heart pacemaker remote mobile monitoring, a reservation remote consultation, a pathological image remote mobile monitoring, a short distance Bluetooth data information exchange, a USB large volume data information exchange, a medical consultation VoIP voice communication, a network emergency recourse; and views a medical materials electronic text, an intelligence recovery game, and a video playing, etc. in the multimedia work status.

Figure 4:
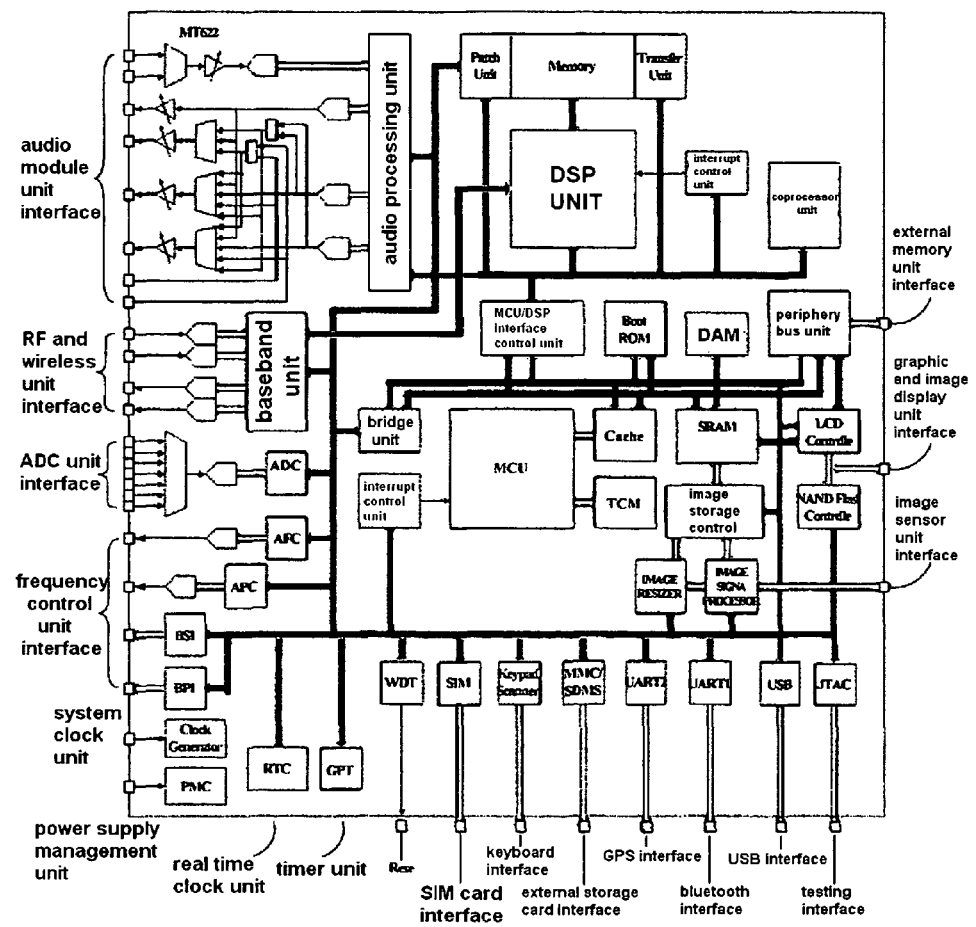
FIG. 4 is an inner structure block diagram of a baseband processor module used in one embodiment of the present invention.

FIG. 4 is the block diagram of the inner structure of the GPRS baseband processor module 100 according to one embodiment of the present invention, which includes at least a microprocessor unit (MCU), a digital signal processor unit, a coprocessor unit, a system bus, a periphery bus, a bridge unit, a periphery bus interface, a data memory unit, a direct access memory DMA unit, a buffer memory unit, a USB controller unit, a power supply management unit, a baseband unit, a frequency control unit, a system clock unit, a real time clock unit, a timer GPT unit, and a periphery instrument and the interface thereof. The periphery instrument and the interface thereof include at least a multiple analog to digital (AD) convertor unit, a keyboard control unit, a graphic and image display control unit, an image collection process unit, an audio process unit, an external data storage card control unit, an external data memory control unit, an asynchronous series communication port UART unit, a USB controller unit, a SIM card control unit, a JTAG test unit, and a radio frequency antenna.

FIGS. 3 and 4 illustrate the relationship between the periphery instruments and the inner function units of the GPRS baseband processor module 100 in accordance with one embodiment of the present invention. The microprocessor unit (MCU) of the GPRS baseband processor module 100 controls the operation of each function unit and periphery instrument. The system clock unit provides the system with a task schedule reference. The real time clock unit provides a data collection timer GPT with a clock source. The power supply management unit provides each function unit and periphery instrument with a power supply. A GPTn in the timer GPT unit generates a required interrupt frequency so as to control a sampling frequency for the analog to digital conversion. The buffer memory unit buffers and stores various data. The baseband unit and the frequency control unit are connected with a radio frequency antenna, so as to control the modulation and the demodulation of the signal and to control the signal conversion between an external radio frequency signal and a baseband unit signal. The SIM card unit is connected to a client identity recognition SIM card so as to provide the mobile network with an identity recognition data of a local host. The multiple analog to digital (AD) convertor unit is connected to the electrophysiological data collection module 101 so as to convert the electrophysiological analog signal to a digital signal. The keyboard control unit is connected to the keyboard module 102 so as to issue various control instructions of the mobile network terminal device and input user information data. The graphic and image display control unit is connected to the graphic and image display module 103, so as to display a human machine interaction interface, a selection list, a medical materials electronic text viewing pages in the multimedia work mode, and so on. The image collection process unit is connected to the image and picture sensor 104 so as to collect the pathological image video data of the user. The audio process unit is connected to a voice communication module 105, so as to enable a VoIP voice communication of the mobile network terminal device and a process of a voice broadcasting of the doctor's advice, the doctor's leave word, and so on. The external data storage card control unit is connected to an external data storage card 106 so as to encode and store respective electrophysiological monitoring data, pathological image video data, and external forward data of the mobile network terminal device by partitions. The external data memory control unit is connected to an external data memory 107 so as to store an application program of the mobile network terminal device, which includes a user information file, a configuration file, user set information data, two dimensional recognition data, medical security data, and so on. A terminal UART1 in the asynchronous series communication port UART unit is connected to a Bluetooth module 108, so as to enable a short distance data information exchange between the mobile network terminal device and an external device. A terminal UART2 is connected to a GPS receiver 110, so as to provide the mobile network terminal device with position information data by a satellite positioning. The USB controller unit is connected to a USB interface module 109, so as to enable a large volume data information exchange between the mobile network terminal device and a computer apparatus. According to the work mode selected in the mobile network terminal device, the GPRS baseband processor module 100 collects and processes the electrophysiological data and the pathological image/picture video data, and achieves various functions simultaneously.

Figure 5:
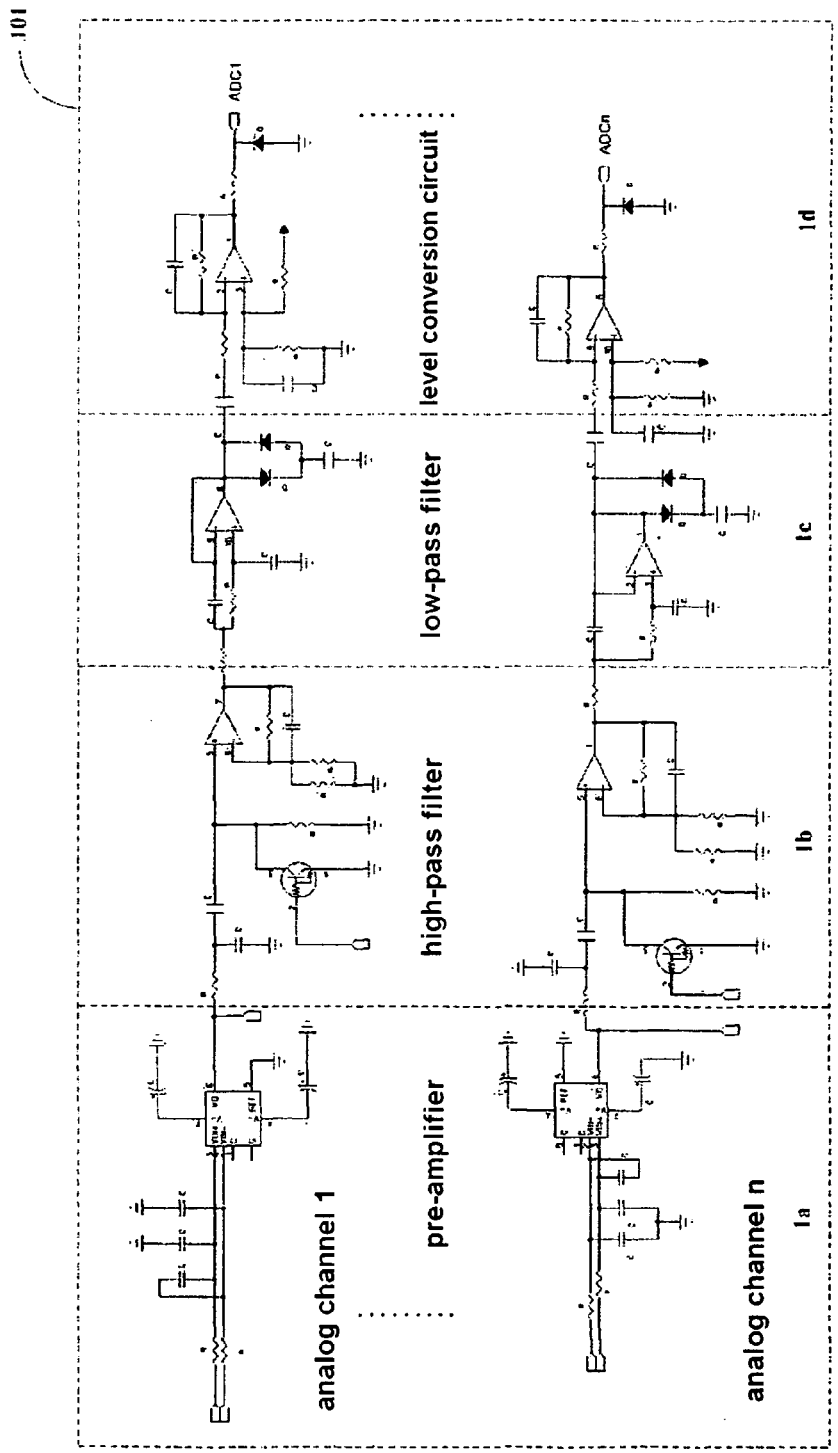
FIG. 5 is a principle block diagram of electrophysiological data collection module used in one embodiment of the present invention.

FIG. 5 illustrates the electrophysiological signal collection module 101 in accordance with one embodiment of the present invention, which includes at least multiple analog signal channels. Each analog signal channel includes a pre-amplifier unit 1a which is comprised of general instrument and meter operation amplifiers, a high-pass filter unit 1b, a low-pass filter unit 1c, and a level conversion unit 1d which are comprised of operation amplifiers. In addition, a pacemaker pulse suppression circuit is provided at the output end of the low-pass filer unit 1c, in order to prevent the pulse voltage "blocking" from influencing the work of followed stages operation amplifiers. The output end of the pre-amplifier unit 1a is connected to the input end of the high-pass filter unit 1b. The output end of the high-pass filter unit 1b is connected to the input end of the low-pass filter unit 1c. The output end of the low-pass filter unit 1c is connected to the input end of the level conversion unit 1d. The output end of the level conversion unit 1d is connected to the input end of each channel of the multiple analog to digital (AD) convertor unit of the baseband processor module 100. The analog signal is converted into a digital signal, and then is sent to the GPRS baseband processor module 100 for processing. The electrophysiological signal collection module 101 may be connected to a plurality of cardiogram sensors, so as to synchronously collect a plurality of cardiogram analog signal data. The cardiogram analog signal data includes, but not limited to, pacemaker pulse signal data, automatic cardioversion ICD pulse signal data. Or the electrophysiological signal collection module 101 may be connected to a cardiogram sensor, a blood pressure sensor, and a breath sensor, so as to synchronously collect the analog signal data of the cardiogram, the blood pressure, and the breath. The electrophysiological signal collection module 101 amplifies, filters, level converts the collected electrophysiological analog signal, and then sends it to the multiple analog to digital (AD) convertor unit of the GPRS baseband processor module 100 for an analog to digital conversion. Since the cardiogram sensor, the blood pressure sensor, the breath sensor and the analog signal processing technologies are all the prior arts, the description thereof is omitted.

In accordance with the sampling frequency setting method of one embodiment of the present invention, the mobile network terminal device sets the interrupt frequency of the timer unit GPTn of the GPRS baseband processor module 100 to be an integer power of 2 by the application program according to the work mode recognition flag, and sets the interrupt call-back function to be a sampling function or a frequency-division sampling function. Each channel of the multiple analog to digital (AD) convertor unit of the GPRS baseband processor module 100 can be set to a same sampling frequency by the sampling function, and can also be set to a different sampling frequency by the frequency-division sampling function. The sampling frequency or the frequency-division sampling frequency of the present invention ranges between 128 Hz and 16,384 Hz. Upon the electrophysiological data monitoring, the sampling frequency of each channel of the multiple analog to digital (AD) convertor unit is at least set at 128 Hz, so as to guarantee that the electrophysiological data will not be distorted. Upon the heart pacemaker monitoring, since the width of the pacemaker pulse is between 0.5 ms and 4 ms, the sampling frequency of the pacemaker pulse channel is required to be set at 2,048 Hz or above. Obviously, the loss of pacemaker pulse data and the automatic cardioversion ICD pulse data can be avoided by increasing the sampling frequency of the pacemaker pulse channel.

In accordance with the sampling frequency setting method of one embodiment of the present invention, the clock source of the timer unit GPTn of the GPRS baseband processor module 100 results from the real time clock unit of the GPRS baseband processor module 100. The main frequency of this real time clock is 32.768 KHz. The automatic frequency division of the timer unit GPTn generates the required interrupt frequency. According to the interruption flag, the multiple analog to digital (AD) convertor unit is activated by the sampling function or the frequency-division sampling function. Data of each channel is read, sent to and stored in the buffer memory unit of the GPRS baseband processor module 100. A record and store flag is sent at regular intervals by the sampling function or the frequency-division sampling function. The microprocessor unit (MCU) of the GPRS baseband processor module 100 performs a storage command, reads data from the buffer memory unit, and then sends it to and stores it in a predetermined region of the external data storage card 106. By means of the frequency-division sampling function, when data of each channel of the multiple analog to digital (AD) convertor unit is read, data of the pacemaker pulse channel is compressed by a corresponding ratio, so as to hold characteristic data and save a storage space. In accordance with the sampling frequency setting method of one embodiment of the present invention, not only does the precise and reliability of the sampling frequency of the electrophysiological data are guaranteed, but also the calculation and subsequent processes are convenient. In addition, frequent calculation of the microprocessor unit (MCU) of the GPRS baseband processor module 100, which causes a sharp rise in the power consumption, can be avoided. A normal operation of the multi-task schedule clock of the Nucleus operation system is maintained.

As illustrated in FIG. 3, in accordance with one embodiment of the present invention, the keyboard module 102 may be connected to the interface of the keyboard control unit of the GPRS baseband processor module 100 in a GPIO parallel manner. Under the control of the application program module 200, the keyboard module 102 issues various control instructions of the mobile network terminal device. The instructions include, but are not limited to, a selection and/or setting of the function status, a selection and/or setting of the work mode, and an input and/or setting of the user information data. The user information data is classified and stored into a user information file and a configuration file of the external data memory 107. The user information data includes, but is not limited to, a fixed IP address of a target server, an access point domain name APN, a user name and password, a SMS number, a MMS address, a VoIP access information, a default target address list, a user identity, a dwelling location, a blood type, a society medical guarantee card number, a medical record summary, a text information. In accordance with one embodiment of the present invention, the keyboard module 102 uses a micro-21 keyboard, and those skilled in the art can also use a customized keyboard.

As illustrated in FIG. 3, in accordance with one embodiment of the present invention, the graphic and image display module 103 is connected to the interface of the graphic and image display control unit of the GPRS baseband processor 100. By means of the application program module 200, the mobile network terminal device controls the graphic and image display module 103 to display a human machine interaction interface, a function selection list, a work status selection list, data, an image, a graphic, a text, a letter, and a medical materials electronic text viewing page, an intelligence recovery game and the like in the multimedia work mode. In addition, a scroll display in real time/freezing various electrophysiological graphics is also possible. Preferably, in the alarm alert status, the graphic and image display module 103 prompts the user by the text and the light on the screen thereof. Preferably, the graphic and image display module 103 in accordance with one embodiment of the present invention uses a high resolution color liquid crystal with a 320×240 array, and a font which is 16 character dot or above, for the viewing and reading of the user.

As illustrated in FIG. 3, in accordance with one embodiment of the present invention, the image and picture sensor 104 is connected to the interface of the image and picture collection process control unit of the GPRS baseband processor module 100. When the mobile network terminal device proceeds into the pathological image monitoring mode, the image and picture sensor 104 is activated by the application program module 200. The image and picture video monitoring time length T is set as N. Focusing automatically, and taking the pathological image and picture video data of the user, compressing the video data, and then sending it to and storing it at the predetermined region of the external data storage card 106. When the pathological image and picture video monitoring time T reaches 0, the mobile network terminal device proceeds into the wait-to-send status automatically. Then the mobile network terminal device registers with the GPRS mobile network according to a sending instruction issued from the user keyboard, establishes a data connection with the target server, sends the pathological image and picture video data, and receives the analysis process comments replied from the target server. Preferably, by means of the instruction issued from the user keyboard, the mobile network terminal device may be controlled to register with the GPRS mobile network during the pathological image monitoring, so as to make a remote real time monitoring of the pathological image video data. Preferably, the image and picture sensor 104 in accordance with one embodiment of the present invention uses a CM571 CMOS camera with 1.3M pixels, the resolution of which can satisfy the requirement of the monitoring for the clinic physic. Those skilled in the art can also use any other video, image, and picture collection devices adapted to the medical monitoring.

As illustrated in FIG. 3, the voice module 105 in accordance with one embodiment of the present invention is comprised of a speaker, an earpiece, and a microphone, which are connected to the interface of the audio process unit of the GPRS baseband processor module 100, so as to enable network voice communication of the mobile network terminal device. When the mobile network terminal device is set to a VoIP voice communication mode, the VoIP access information and the default target address stored in the external data memory 107 are read by the application program module 200 according to the work mode flag, a call establishing request is launched, the callee responds to this request, and then the user makes voice medical consultation or voice communication with the callee at the target end over the GPRS mobile network by the speaker and the earpiece of the voice module 105. Preferably, the default target address can be set as an address of a target hospital electrophysiological remote guardianship center solely, and can also be set to be a plurality of target addresses involving the relatives of the user. Preferably, the call establishing request is sent for those target addresses circularly.

When the mobile network terminal device is set to a voice report function, under the control of the application program module 200, the voice module 105 can voice report the doctor's advice on diagnosis and process, a doctor's leave word, a medical log content preset by the user, and an alarm alert replied by the target server. Preferably, the voice module 105 can play an audio in the multimedia work mode. Preferably, in accordance with one embodiment of the present invention, the voice module 105 uses a general micro speaker, a general earpiece, and a general microphone.

As illustrated in FIG. 3, in accordance with one embodiment of the present invention, the external data storage card 106 is connected to the interface of the external data storage card control unit of the GPRS baseband processor module 100. By the application program module 200, the mobile network terminal device controls the external data storage card 106 to be divided into a continuous electrophysiological data storage area, an abnormal electrophysiological data storage area, a pathological image video data storage area, an external forward data storage area, a position information data storage area, a multimedia data storage area, which are respectively used for storing 24 hours continuous electrophysiological data, abnormal electrophysiological data, pathological image video data, external forward data, position information data, multimedia data, various analysis and diagnosis parameter information, and statistic information of the mobile network terminal device. Preferably, the external data storage card 106 in accordance with one embodiment of the present invention uses a Kingston TF card of 512M capacity, in which the electrophysiological continuous data storage area can store continuous monitoring data for more than 168 hours, the abnormal electrophysiological data storage area can store abnormal electrophysiological data of 24 KB for more than 2000 frames. Those data further comprises analysis and diagnosis parameter information, and statistic information; and can also provide the clinic doctors with a plurality of 24 hours continuous monitoring data for quantitatively analyzing the disorder of the heart rhythm and the lack of blood of the cardiac muscle, i.e., the Holter analysis of a dynamic cardiogram monitoring used usually in the cardiac department of the hospital. It fully satisfies the requirement of a qualitative analysis and a quantitative analysis on the heart electrophysiological data for the clinic doctors and the users.

As illustrated in FIG. 3, in accordance with one embodiment of the present invention, the external data memory 107, which is used to store the application program module 200 (including a user information file and a configuration file), user setting information data, two dimensional code recognition data, and medical evidence data, etc., is connected to the interface of the external data memory control unit of the GPRS baseband processor module 100. The user setting information data includes, but is not limited to, a target server fixed IP address, an access point domain name APN, a user name and password, a SMS number, a MMS address, a VoIP access information, a default target address list, a user identity, a dwelling location, a blood type, a society medical guarantee card number, a medical record summary, a text information, and a function setting information data, etc. The user information data is used to a wireless access and data information exchange of the network level of the mobile network terminal device, and is used to the identity authentication in the data exchange and the provision of the brief medial history. In addition, the user information data is also used to establish a VoIP voice communication channel between the mobile network terminal device and the callee at the target end, so as to enable voice medical consultation. The medical evidence data is operation information data of the mobile network terminal device, and includes, but is not limited to, an electrophysiological monitoring mode and date/time, an alarm content and date/time, a sent data content and date/time, a network connection count/status and date/ time, received doctor advice and date/time, a content responded to a control command and date/time, an emergency recourse event date/time and response date/time. The medical evidence data is circularly stored, and can not be deleted manually by the user. Preferably, in accordance with one embodiment of the present invention, the external data memory 107 uses a Flash S71PL12xN.

The method of the medical evidence data can be the medical security data method disclosed in Chinese patent application No. 200610000895.4.

As illustrated in FIG. 3, in accordance with one embodiment of the present invention, the Bluetooth module 108 is connected to the UART1 interface in the asynchronous series communication port UART unit of the GPRS baseband processor module 100, which is used for a short distance data information exchange of the mobile network terminal device. When the mobile network terminal device proceeds into the short distance data communication mode, the Bluetooth module 108 is controlled and activated by the application program module 200. The Bluetooth module 108 sends a paging, establishes a data linkage to the external device, and then sends the data information stored in the mobile network terminal device to the external device. Meanwhile, the Bluetooth module 108 can receive the data information including the medical data information sent from the external device, and store it in the predetermined area of the external data storage card 106. Upon required, the mobile network terminal device can forward those data from the external device to the target server. The external device includes, but is not limited to, a Bluetooth printer, a Bluetooth digital cell phone, a Bluetooth smart device, a local area network and a wide area network with a Bluetooth interface. Preferably, in accordance with one embodiment of the present invention, the Bluetooth module 108 uses a MT 6601 Bluetooth baseband processor.

As illustrated in FIG. 3, in accordance with one embodiment of the present invention, the USB interface module 109 is connected to the interface of the USB controller unit of the GPRS baseband processor module 100, so as to enable the connection of the mobile network terminal device with a USB interface of an external computer apparatus. Therefore, it is possible to exchange a large volume of data information, download a large volume of data information stored in the mobile network terminal device, or install a medical materials electronic text, an intelligence recovery game, a heart anabiosis teaching video clip, and so on for the mobile network terminal device. Preferably, in accordance with one embodiment of the present invention, the USB interface module 109 uses a general micro USB plug MINI-USB 8P.

As illustrated in FIG. 3, in accordance with one embodiment of the present invention, the GPS receiver module 110 is connected to the UART2 interface in the asynchronous series communication port UART unit of the GPRS baseband processor module 100, which is used for the satellite positioning of the mobile network terminal device so as to obtain the information on the position where the mobile network terminal device is located. The information on the position includes longitude, latitude, and ellipse height data. The position information is sent to and stored in the position information storage area of the external data storage card 106, so as to provide the remote server with the information on the position where the user is located while exchanging the network data. Preferably, in accordance with one embodiment of the present invention, the GPS receiver module 110 uses a SE8901 GPS receiver dedicated for a handhold device.

In accordance with one embodiment of the present invention, the power supply management unit of the GPRS baseband processor module 100 provides each function unit and periphery instrument with the power supply of +3.3V, −3.3V, +2.8V, +1.8V, +1.2V respectively. In the heart pacemaker monitoring mode, the mobile network terminal device turns off the power supply of the radio frequency antenna of the GPRS baseband processor module 100 by the application program module 200, in order to prevent the radio frequency radiation from interfering with the normal work of the pacemaker and the automatic cardioversion IDC. In the electrophysiological data special monitoring mode, the mobile network terminal device turns off the power supply of the radio frequency antenna and the power supplies of the voice module 105 by the application program module 200, and keeps monitoring the electrophysiological data, such that the user can use the mobile network terminal device in special situations of being in flight, in conference, and the inhibition of the mobile device, etc. Therefore, the device and method according to the present invention can maintain the continuity of the electrophysiological data monitoring, and can prevent the user from suffering the cardiac accidents in those special situations.

In accordance with one embodiment of the present invention, preferably, the MT6225 GPRS baseband processor module is used, and the baseband processor module of other standards can also be used.

In accordance with one embodiment of the present invention, the Nucleus embedded operation system is used. In addition, the embedded operation system such as Windows mobile, Android, Linux, Palm OS, Symbian, OSE, Hopen, and so on, and the updated version thereof can also be used.

In accordance with one embodiment of the present invention, the general 1,000 mAh rechargeable lithium battery is used as the work power supply, the average power consumption of the mobile network terminal device is not higher than 70 mW, and the time for continuous usage is longer than 48 hours. The whole machine is encapsulated into a small housing, has a small volume and a light weight. In addition, the device according to the present invention is easy and convenient to be operated, and can be used as a medical information tool of the user individual which is adapted to be carried and used for a long term.

FIGS. 6-15 illustrate a method for monitoring electrophysiological data and a pathological image according to the present invention. The method involves running an application program module 200 in an operation system, controlling and setting a work mode of the mobile network terminal device. The work mode includes an electrophysiological data monitoring mode, an electrophysiological data special monitoring mode, a heart pacemaker monitoring mode, a reservation remote consultation mode, a pathological image monitoring mode, a short distance data communication mode, a VoIP voice communication mode, and a network emergency recourse mode. Particularly, the method includes the steps of:

[1] the work mode of the mobile network terminal device is selected and/or set according to instructions generated from operating a keyboard by a user, and a work mode recognition flag is sent;

[2] when the electrophysiological data monitoring mode is selected in step [1], according to the work mode recognition flag, the mobile network terminal device sets the interrupt frequency of the timer unit GPTn of the GPRS baseband processor module 100 to be an integer power of 2, sets the interrupt callback function to be the sampling function, and sets the sampling frequency to be at least 128 Hz by the application program module 200;

[3] in step [2], the mobile network terminal device reads the access point domain name APN and the target server IP address simultaneously, registers with the mobile network, establishes a data connection to the target server, and sends a local host user flag and a service category request flag;

[4] according to a response flag replied from the target server, the mobile network terminal device controls the microprocessor unit (MCU) of the GPRS baseband processor module 100 to enter a sleep state, and keeps an online network connection by the application program module 200;

[5] data of each channel of the multiple analog to digital (AD) convertor unit of the GPRS baseband processor module 100 is read by the sampling function according to the preset sampling frequency, and the electrophysiological data is sent to and stored in the buffer memory unit of the GPRS baseband processor module 100;

[6] the record storage flag is regularly sent by the sampling function, and the microprocessor unit (MCU) of the GPRS baseband processor module 100 performs a storage command, reads data from the buffer memory unit, and then sends the data to and stores the data in a preset area of the external data storage card 106;

[7] the electrophysiological data is analyzed by the application program module 200, if the electrophysiological data exceeds an alert threshold, an alarm flag will be set, and an audio alert and/or a vibration alert, a light alert, and a text alert will be sent;

[8] according to the alarm category flag, the mobile network terminal device reads event data stored in the external data memory card 106, packetizes the data, and makes a data/information exchange over the network under the control of the application program module 200;

[9] the target server sends a command online, and the mobile network terminal device performs instructions of the target server according to the target server command flag.

Preferably, the method further includes the steps of:

[10] when the electrophysiological data special monitoring mode is selected in step [1], according to the work mode recognition flag, the mobile network terminal device turns off the power supplies of the voice module 105 and the radio frequency antenna unit of the GPRS baseband processor module 100 under the control of the application program module 200;

[11] in step [10], the mobile network terminal device sets the interrupt frequency of the timer unit GPTn of the GPRS baseband processor module 100 to be an integer power of 2, sets the interrupt callback function to be the sampling function, and sets the sampling frequency to be at least 128 Hz;

[12] data of each channel of the multiple analog to digital (AD) convertor unit of the GPRS baseband processor module 100 is read by the sampling function according to the preset sampling frequency, and the electrophysiological data is sent to and stored in the buffer memory unit;

[13] the record storage flag is regularly sent by the sampling function, and the microprocessor unit (MCU) of the GPRS baseband processor module 100 performs a storage command, reads data from the buffer memory unit, and then sends the data to and stores the data in a preset area of the external data storage card 106;

[14] the electrophysiological data is analyzed by the application program module 200, if the electrophysiological data exceeds an alert threshold, an alarm category flag will be set, an vibration alert and/or a light alert, and a text alert will be sent, and the user will be prompted to operate the keyboard so as to launch a network data communication function;

[15] according to instructions from the user keyboard, the mobile network terminal device activates the radio frequency antenna unit of the GPRS baseband processor module 100, reads the access point domain name APN and the target server IP address, registers with the mobile network, establishes the data connection to the target server, and sends the local host user flag and the service category request flag;

[16] according to the response flag replied from the target server, the mobile network terminal device reads event data stored in the external data memory card 106, packetizes the data, and makes a data/information exchange over the network under the control of the application program module 200.

Preferably, the method further includes the steps of:

[17] when the heart pacemaker monitoring mode is selected in step [1], according to the work mode recognition flag, the mobile network terminal device turns off the power supply of the radio frequency antenna unit of the GPRS baseband processor module 100 under the control of the application program module 200;

[18] in step [17], the mobile network terminal device raises the interrupt frequency of the timer unit GPTn of the GPRS baseband processor module 100 simultaneously, sets the interrupt frequency to be the integer power of 2, sets the interrupt callback function to be the frequency-division sampling function, sets the sampling frequency of the pacemaker pulse channel to be at least 2,048 Hz, and sets the sampling frequency of the cardiogram data channel to be at least 128 Hz;

[19] data of each channel of the multiple analog to digital (AD) convertor unit of the GPRS baseband processor module 100 is read by the frequency-division sampling function according to the preset frequency-division sampling frequency, the pacemaker pulse data is compressed, and then sent to and stored in the buffer memory unit;

[20] the record storage flag is regularly sent by the frequency-division sampling function, and the microprocessor unit (MCU) of the GPRS baseband processor module 100 performs a storage command, reads data from the buffer memory unit, and then sends the data to and stores the data in a preset area of the external data storage card 106;

[21] the pacemaker pulse data is analyzed by the application program module 200, if the pacemaker data exceeds an alert threshold, an alarm category flag will be set, an audio alert and/or a vibration alert, a light alert, and a text alert will be sent, and the user will be prompted to operate the keyboard so as to launch a network data communication function;

[22] according to instructions from the user keyboard, the mobile network terminal device activates the radio frequency antenna unit of the GPRS baseband processor module 100, reads the access point domain name APN and the target server IP address, registers with the mobile network, establishes the data connection to the target server, and sends the local host user flag and the service category request flag;

[23] according to the response flag replied from the target server, the mobile network terminal device reads event data stored in the external data memory card 106, packetizes the data, and makes a data/information exchange over the network under the control of the application program module 200.

Preferably, the method further includes the steps of:

[24] when the reservation remote consultation mode is selected in step [1], according to the work mode recognition flag, the mobile network terminal device sets wake up time T of the real time clock unit of the GPRS baseband processor module 100;

[25] when it reaches the preset time T of the real time clock unit, an activation signal flag will be sent;

[26] according to the activation signal flag, the mobile network terminal device reads the access point domain name APN and the target server IP address, registers with the mobile network, establishes the data connection to the target server, and sends the local host user flag and the service category request flag;

[27] according to the response flag replied from the target server, the mobile network terminal device reads data stored in the external data memory card 106, packetizes the data, and makes a data/information exchange over the network under the control of the application program module 200.

Preferably, the method further includes the steps of:

[28] when the pathological image monitoring mode is selected in step [1], according to the work mode recognition flag, the mobile network terminal device sets the pathological image monitoring time length T, and activates the image and picture sensor 104;

[29] the image and picture sensor 104 focuses automatically, takes the pathological image video data of the user, and then sends the data to and stores the data in a preset area of the external data storage card;

[30] when it reaches the pathological image monitoring preset time T, the mobile network terminal device goes into the wait-to-send status;

[31] according to the sending instruction issued from the user keyboard, the mobile network terminal device reads the access point domain name APN and the target server IP address, registers with the GPRS mobile network, establishes the data connection to the target server, and sends the local host user flag and the service category request flag;

[32] according to the response flag replied from the target server, the mobile network terminal device reads video data stored in the external data memory card 106, compresses a data packet, and makes a data/information exchange over the network under the control of the application program module 200.

Preferably, the method further includes the steps of:

[33] when the short distance data communication mode is selected in step [1], according to the work mode recognition flag, the mobile network terminal device activates the Bluetooth module 108 to send a paging signal to the external device;

[34] according to a Bluetooth response flag "device access code DAC" of the external device, the Bluetooth module 108 of the mobile network terminal device sends a FH synchronization packet, exchanges real time clock and flag information, and establishes a data channel connection;

[35] the mobile network terminal device reads the data stored in the external data memory card 106 under the control of the application program module 200, and makes a short distance data/information exchange;

[36] the Bluetooth module 108 of the mobile network terminal device receives the data/information sent from the external device, sends the data/information to and stores the data/information in a preset area of the external data storage card 106 under the control of the application program module 200;

[37] according to forward instructions issued from operating the keyboard by the user, the mobile network terminal device reads the access point domain name APN and the target server IP address, registers with the GPRS mobile network, establishes the data connection to the target server, and sends the local host user flag and the service category request flag;

[38] according to the response flag replied from the target server, the mobile network terminal device reads data stored in the external data memory card 106, packetizes the data, and forwards data of the external device under the control of the application program module.

Preferably, the method further includes the steps of:

[39] when the VoIP voice communication mode is selected in step [1], according to the work mode recognition flag, the mobile network terminal device activates the voice module 105, and registers with the GPRS mobile network simultaneously;

[40] the mobile network terminal device calls the VoIP voice communication protocol by the application program module 200, reads a VoIP access information and a default target address stored in the external data memory 107, and initiates a request for establishing a call;

[41] a callee at the target end makes response to the request, and the mobile network terminal device and the callee at the target end make voice medical consultation or voice communication.

Preferably, the method further includes the steps of:

[42] when the network emergency recourse mode is selected in step [1], according to the work mode recognition flag, the mobile network terminal device sets the alarm category flag by the application program module 200, and sends an audio alert and/or a vibration alert and a light alert;

[43] the mobile network terminal device reads the access point domain name APN and the target server IP address stored in the external data memory 107, registers with the GPRS mobile network, establishes the data connection to the target server, and sends the local host user flag, a request flag "I need help", and position information data;

[44] according to the response flag replied from the target server, the mobile network terminal device quits the network emergency recourse work mode.

The work procedure of the present invention will be described in detail in connection with the drawings in the following.

Figure 6:
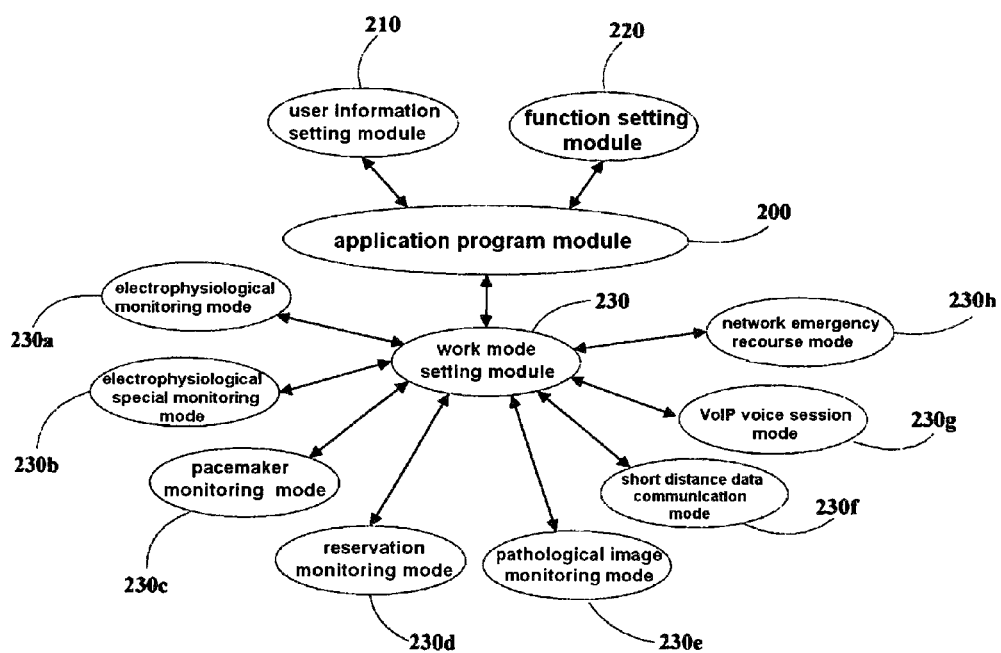
FIG. 6 is a structure diagram of an application program module for controlling the operation of the mobile network terminal device according to one embodiment of the present invention.

FIG. 6 illustrates a structure of the application program module 200 for controlling the operation of the mobile network terminal device according to one embodiment of the present invention, which comprises:

a user information/data setting module 210, which is responsible for controlling the mobile network terminal device to set and install a domain name, an address, a password, and a user name required by a wireless access on the network level, and a medical record summary and a society medical insurance card number required by the analysis and diagnosis, etc.;

a function setting module 220, which is responsible for controlling the function setting of the mobile network terminal device, including a selection of the text category, a selection of a voice report, turning on and off of an audio alert, a setting of a high or low volume, a setting of the screen color and luminance of the image and graphic display module, a setting of the multimedia function status, a clearance of the data, and so on;

a work mode setting module 230, which is responsible for controlling the selection of various work modes of the mobile network terminal device.

Figure 7:
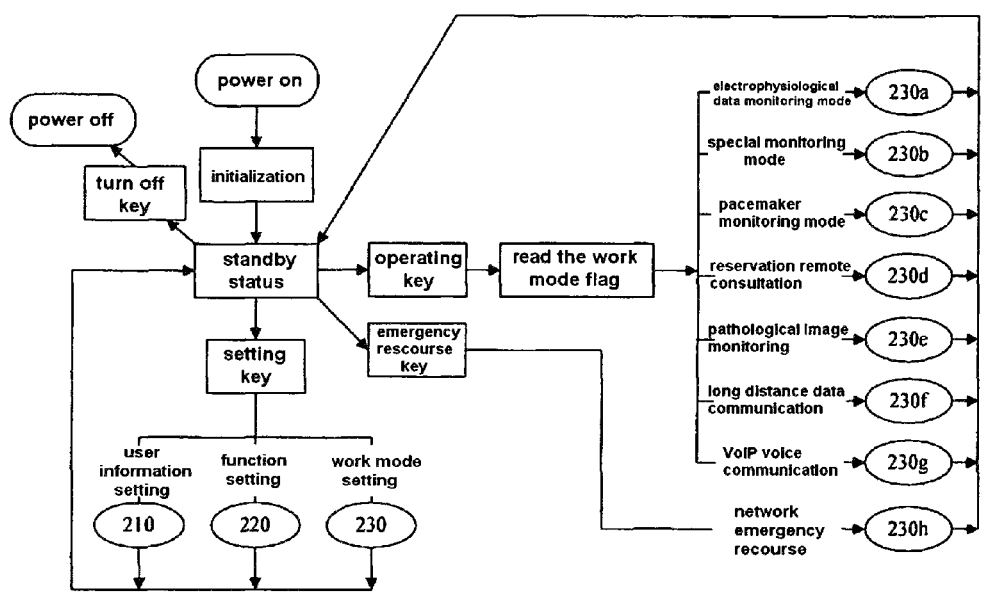
FIG. 7 is a flow chart illustrating the main program of the application program module for controlling the operation of the mobile network terminal device according to one embodiment of the present invention.

FIG. 7 is a flow chart for the main program of the application program module 200 for controlling the operation of the mobile network terminal device according to one embodiment of the present invention. As illustrated in FIG. 7, the mobile network terminal device proceeds into an initiation and a self test after power-on, and enters a standby status. In the standby status, if a "setting key" is triggered, the mobile network terminal device will proceed into a setting status. Under this status, a user information/data setting 210, a function setting 220, and a work mode setting 230 can be selected so as to make a corresponding setting. After completing the setting, the mobile network terminal device returns to the standby status. If the work mode does not be selected and/or set, a default work mode is electrophysiological data monitoring mode 230a. In the standby status, if a "running key" is triggered, the mobile network terminal device will operate according to the work mode flag. In the standby status, if a "emergency recourse key" is triggered, the mobile network terminal device will proceed into a network emergency recourse work mode 230h, and send the recourse information "I need help" to the preset target address. In the standby status, if a "power-off key" is triggered, the mobile network terminal device will turn off the power supply, and stop operating.

Figure 8:
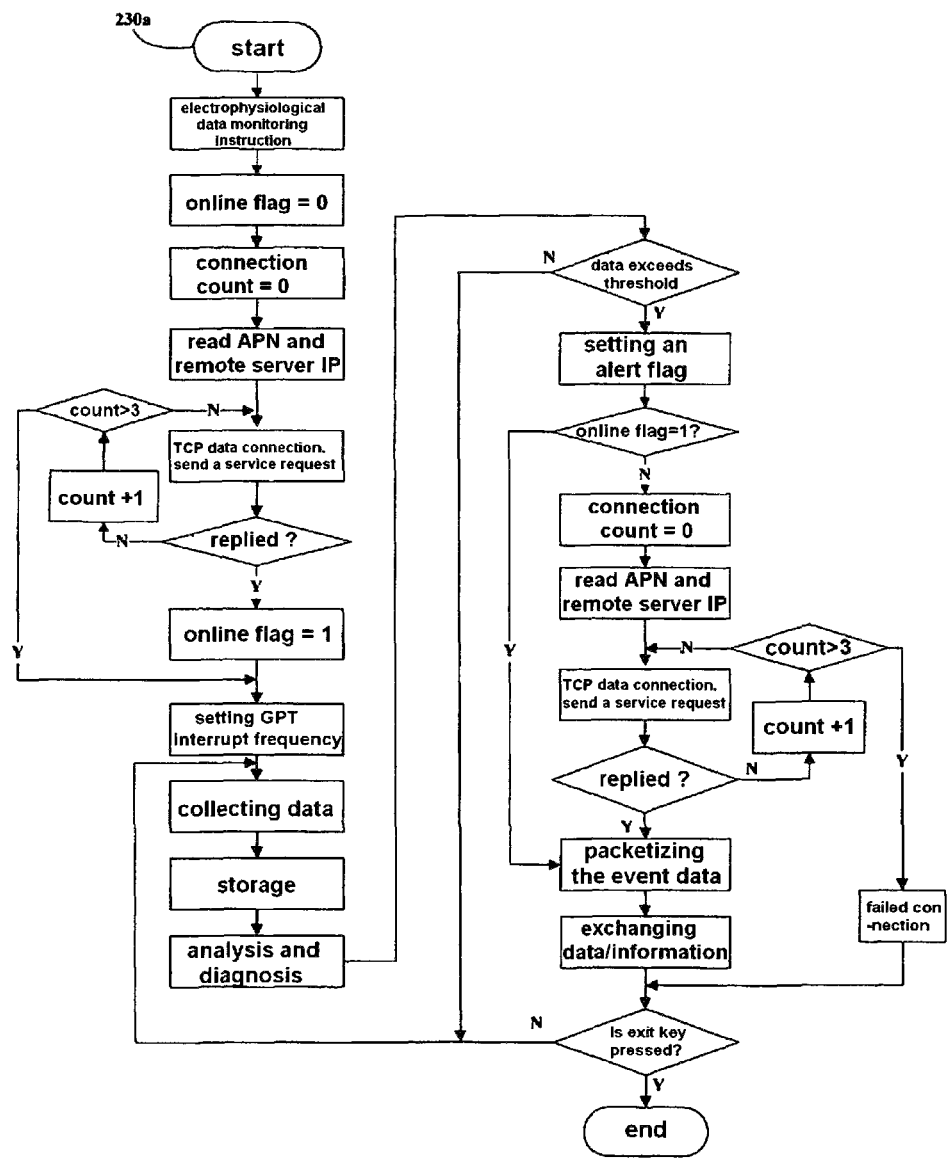
FIG. 8 is a flow chart illustrating the process steps of the mobile network terminal device in the electrophysiological data monitoring mode.

FIG. 8 is a flow chart illustrating the process steps of the mobile network terminal device in the electrophysiological data monitoring mode. The mobile network terminal device proceeds into electrophysiological data monitoring work status 230a, set the previous network online flag to be zero according to the work mode flag, reads an access point domain name APN and a remote target server IP address stored in the external data memory 107, registers with the GPRS mobile network, establishes a data connection to the target server, and sends a local host user flag and a service category request flag to the target server. The mobile network terminal device sets the network online flag to be 1 according to a response flag replied from the remote target server, controls the microprocessor unit (MCU) of the GPRS baseband processor 100 to enter a sleep status, maintains a network online connection. Meanwhile, the mobile network terminal device sets the interrupt frequency of the timer unit GPTn of the GPRS baseband processor module 100 to be an integer power of 2, sets the interrupt callback function to be the sampling function, and can sets the sampling frequency to be at least 128 Hz. Data of each channel of the multiple analog to digital (AD) convertor unit is read by the sampling function according to the preset sampling frequency, and the data is sent to and stored in the buffer memory unit. The record storage flag is regularly sent by the sampling function, and the microprocessor unit (MCU) performs a storage command, reads data from the buffer memory unit, and then sends the data to and stores the data in a preset area of the external data storage card 106. In certain case, if the mobile network terminal device registers with the GPRS mobile network for three times continuously and does not receive the response flag replied from the target server each time, sets the network online flag to be 0 and keeps monitoring the electrophysiological data.

When the electrophysiological data is analyzed and determined to exceed an alert threshold, the mobile network terminal device sets an alarm category flag, and sends an audio alert and/or a vibration alert, a light alert, and a text alert. At the same time, the mobile network terminal device checks whether the network online flag is 1 or not. If the network online flag is 1, the data is packetized, the monitoring data packet is sent, an analysis process suggestion returned from the target server is received, and the network data information exchange is completed. Thus, the mobile network terminal device goes into a status for selecting to exit the electrophysiological data monitoring. If exiting the electrophysiological data monitoring has not been selected for several seconds, the electrophysiological data monitoring proceeds automatically. Otherwise, the work flow is ended. In addition, if the network online flag is 0, the network is not in a connection status, and the mobile network terminal device registers again to establish a connection, sends a monitoring data packet, and receives the analysis process suggestion returned from the target server. If the mobile network terminal device registers with the GPRS mobile network for three times continuously and does not receive the response flag replied from the target server each time, a network connection failure flag is set, and the user is prompted that the network connection is failed. During the electrophysiological data monitoring, the user can end the monitoring work flow by pressing the exit key.

In accordance with one embodiment of the present invention, the target server can send a command and data online, control the mobile network terminal device to perform the command of the target server. The command sent by the target server includes a function setting command, a work status determination command, an command for obtaining data/information within the device, a service category response command, an abnormal event alarm command. According to the present invention, a passive monitoring mode in prior art is changed, and the doctors can understand conveniently the work condition of the current "active" mobile network terminal device at the target server.

Figure 9:
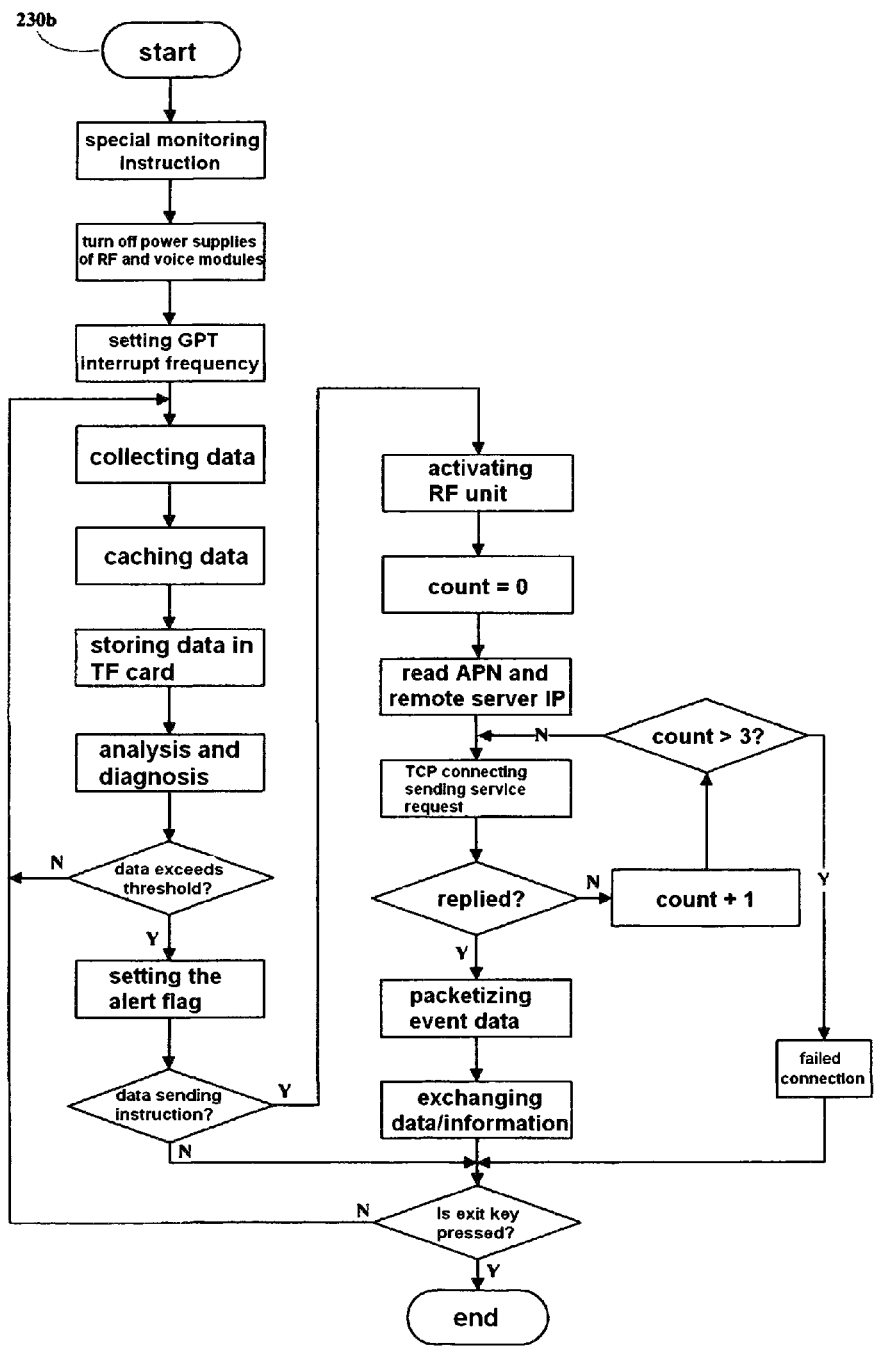
FIG. 9 is a flow chart illustrating the process steps of the mobile network terminal device in the electrophysiological data special monitoring mode.

FIG. 9 is a flow chart illustrating the process steps of the mobile network terminal device in the electrophysiological data special monitoring mode. The mobile network terminal device proceeds into the electrophysiological data special monitoring work status 230b, turns off the power supplies of the voice module 105 and the radio frequency antenna unit of the GPRS baseband processor module 100 according to the work mode flag. Meanwhile, the mobile network terminal device sets the interrupt frequency of the timer unit GPTn to be an integer power of 2, sets the interrupt callback function to be the sampling function, and can sets the sampling frequency to be at least 128 Hz. Data of each channel of the multiple analog to digital (AD) convertor unit of the GPRS baseband processor module 100 is read by the sampling function according to the preset sampling frequency, and the electrophysiological data is sent to and stored in the buffer memory unit. The record storage flag is regularly sent by the sampling function, and the microprocessor unit (MCU) performs a storage command, reads data from the buffer memory unit, and then sends the data to and stores the data in a preset area of the external data storage card 106. When the electrophysiological data exceeds an alert threshold, the mobile network terminal device sets an alarm category flag, and sends a vibration alert and/or a light alert, and a text alert, so as to prompt the user to operate the keyboard module 102 and activate the network data communication function. The mobile network terminal device activates the radio frequency antenna unit of the GPRS baseband processor module 100 according to the instruction sent by the keyboard of the user, sets the previous network connection count to be zero at the same time, reads the access point domain name APN and the target server IP address stored in the external data memory 107, registers with the GPRS mobile network, establishes a data connection to the target server, sends the local host user flag and the service category request flag. According to the response flag replied from the target server, the mobile network terminal device reads the event data stored in the external data storage card 106, packetizes the data, and makes a data/information exchange over the network. If there is no response from the target server, the mobile network terminal device will increase a network connection count by 1, and determine whether the network connection count is greater than 3. If the network connection count is greater than 3, the user is prompted that a network connection is failed. During the electrophysiological data special monitoring, the user can end the special monitoring work flow by pressing the exit key.

In accordance with one embodiment of the present invention, the power supplies of the voice module 105 and the radio frequency antenna unit of the GPRS baseband processor module 100 are turned off. The mobile network terminal device is in an offline and silent status, which is convenient for the user to use the mobile network terminal device in the occasions such as an air plane flight, a conference, and an inhibition of the mobile device. Therefore, the continuity of the electrophysiological data monitoring can be maintained, and the electrophysiological abnormity of the user in those special occasions can be detected in time.

Figure 10:
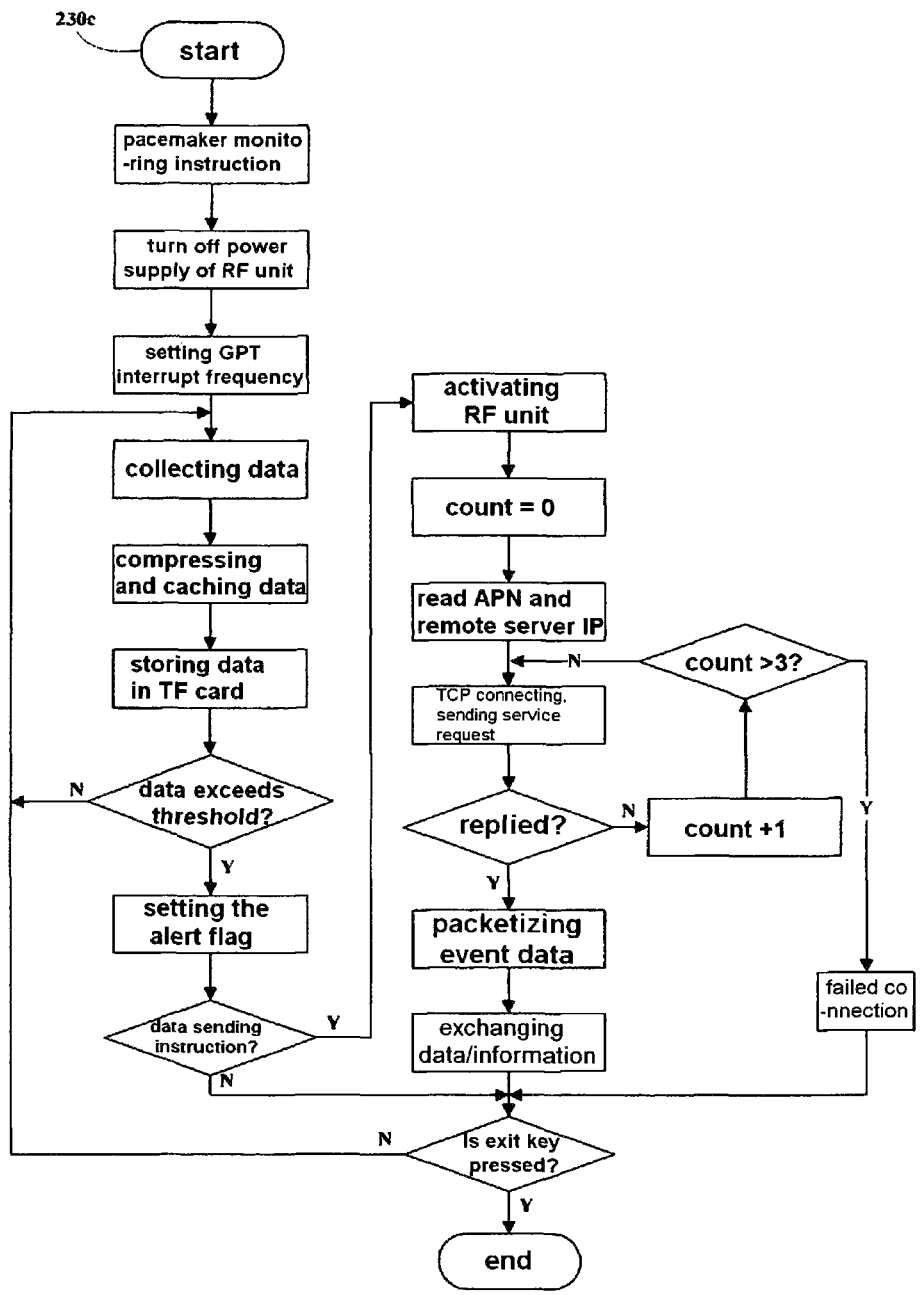
FIG. 10 is a flow chart illustrating the process steps of the mobile network terminal device in the heart pacemaker monitoring mode.

FIG. 10 is a flow chart illustrating the process steps of the mobile network terminal device in the heart pacemaker monitoring mode. The mobile network terminal device proceeds into a heart pacemaker monitoring work status 230c. According to the work mode flag, the mobile network terminal device turns off the power supply of the radio frequency antenna unit of the GPRS baseband processor module 100, and raises the interrupt frequency of the timer unit GPTn simultaneously, sets the interrupt frequency to be the integer power of 2, sets the interrupt callback function to be the frequency-division sampling function. By the frequency-division sampling function, the sampling frequency of the pacemaker pulse channel is set to be at least 2,048 Hz, and the sampling frequency of the cardiogram signal channel is set to be at least 128 Hz. The multiple analog to digital (AD) convertor unit of the GPRS baseband processor module 100 is activated according to the preset frequency-division sampling frequency by the frequency-division sampling function, and data of each channel is read. The pacemaker pulse data is compressed, and then sent to and stored in the buffer memory unit. The record storage flag is regularly sent by the frequency-division sampling function. The microprocessor unit (MCU) of the GPRS baseband processor module 100 performs a storage command, reads data from the buffer memory unit, and then sends the data to and stores the data in a preset area of the external data storage card 106. Since the amount of the pacemaker pulse data is large, the data is compressed for storage by a corresponding ratio, which reduces the storage space occupied by the data effectively. When the pacemaker pulse data exceeds an alert threshold, the mobile network terminal device sets an alarm category flag, sends an audio alert and/or a light alert, and a text alert, so as to prompt the user to enable a network data communication function by operating the keyboard. The mobile network terminal device activates the radio frequency antenna unit according to the sending instruction sent from the user keyboard, sets the previous network connection count to be zero at the same time, reads the access point domain name APN and the target server IP address stored in the external data memory 107, registers with the GPRS mobile network, establishes the data connection to the target server, sends the local host user flag and the service category request flag, reads the event data stored in the external data storage card 106, packetizes the data, and makes the data/information exchange over the network. If the target server does not make a response, the mobile network terminal device will increase the network connection count by 1, and determine whether the network connection count is greater than 3. If the network connection count is greater than 3, the user will be prompted that the network connection is failed. During the heart pacemaker monitoring, the user can end the heart pacemaker monitoring work flow by pressing the exit key.

In accordance with one embodiment of the present invention, the raising of the sampling frequency of the pacemaker pulse channel can avoid the missing of the pacemaker pulse data. Therefore, it is benefit to make a calculation and an analysis so as to provide the clinic diagnosis by the remote server and clinic doctors. Meanwhile, the power supply of the radio frequency antenna unit is turned off during the heart pacemaker monitoring, which effectively prevents the radio frequency radiation from interfering with the normal work of the heart pacemaker including the automatic cardioversion IDC. The problem that the existing technology can not be used to the heart pacemaker monitoring and the automatic cardioversion IDC monitoring is solved well.

The electrophysiological data analysis and alert method illustrated in FIGS. 8-10 can be the electrophysiological self-adaptive analysis method disclosed in the Chinese patent application No. 200610000895.4.

Figure 11:
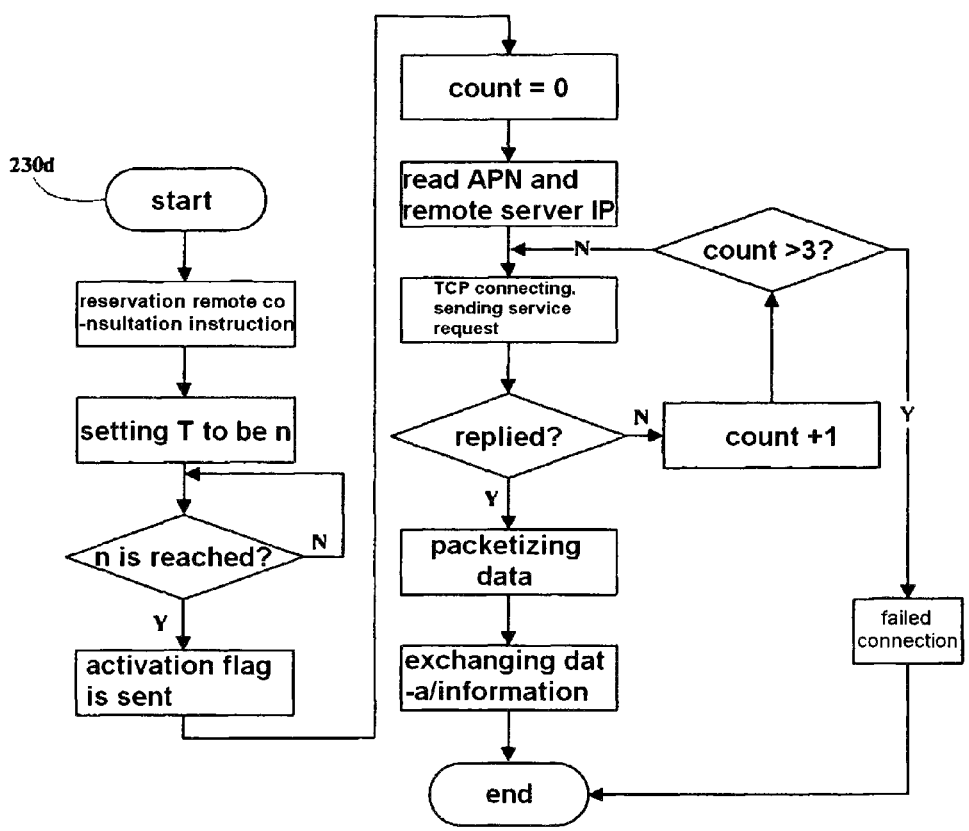
FIG. 11 is a flow chart illustrating the process steps of the mobile network terminal device in the reservation remote consultation mode.

FIG. 11 is a flow chart illustrating the process steps of the mobile network terminal device in the reservation remote consultation mode. The mobile network terminal device proceeds into the reservation remote consultation work status 230d. According to the work mode flag, the mobile network terminal device sets the wake up time T of the real time clock unit of the GPRS baseband processor module 100 to be N. When the preset time T of the real time clock unit is reached, an activation signal flag is sent. According to the activation signal flag, the mobile network terminal device sets the previous network connection count to be zero, reads the access point domain name APN and the target server IP address stored in the external data memory 107, registers with the GPRS mobile network, establishes the data connection to the target server, sends the local host user identity flag and the service category request flag. According to the response flag replied from the target server, the mobile network terminal device reads the data stored in the external data storage card 106, packetizes the data, and makes a data/information exchange over the network. If the target server does not make a response, the mobile network terminal device will increase the connection count by 1, and determine whether the network connection count is greater than 3. If the connection count is greater than 3, the user is prompted that the network connection is failed, and the work flow is ended.

In accordance with one embodiment of the present invention, in the reservation remote consultation mode, the user can make a summary reservation remote consultation for the monitoring data in his or her certain time period, and can also make a reservation remote consultation for the monitoring data at a certain time.

Figure 12:
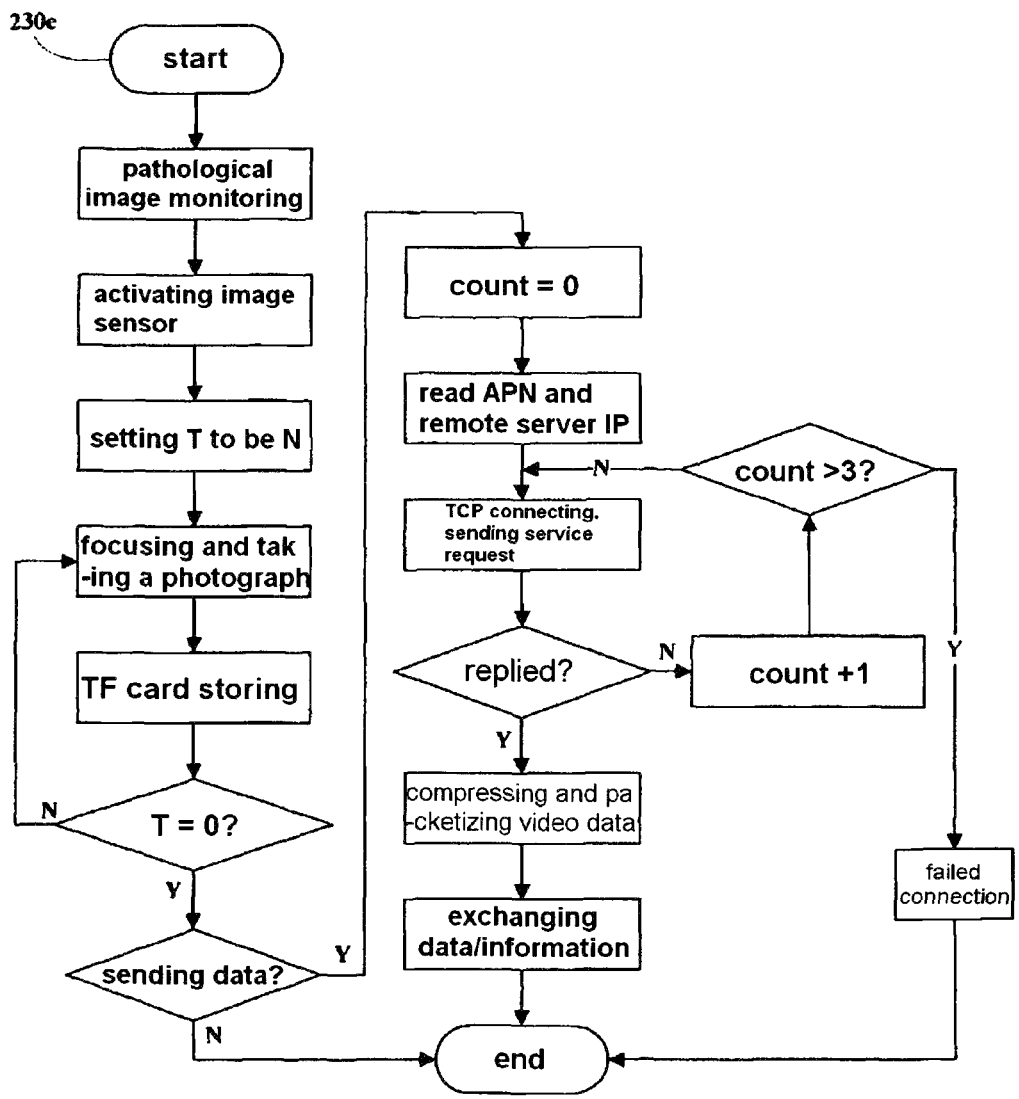
FIG. 12 is a flow chart illustrating the process steps of the mobile network terminal device in the pathological image monitoring mode.

FIG. 12 is a flow chart illustrating the process steps of the mobile network terminal device in the pathological image monitoring mode. The mobile network terminal device proceeds into the pathological image monitoring work status 230e. According to the work mode flag, the mobile network terminal device activates the image sensor 104, sets the pathological image monitoring time length T to be N. The image sensor 104 focuses automatically, takes the pathological image and picture of the user, and then sends the image and picture to and stores the image and picture in the preset area of the external data storage card 106. When the set pathological image monitoring time T is reached, the mobile network terminal device enters a wait-to-send status automatically. According to the sending instruction sent from the user keyboard, the mobile network terminal device sets the previous network connection count to be zero, reads the access point domain name APN and the target server IP address stored in the external data memory 107, registers with the GPRS mobile network, establishes the data connection to the target server, sends the local host user flag and the service category request flag. According to the response flag replied from the target server, the mobile network terminal device reads the video data stored in the external data storage card 106, compresses and packetizes the data, and makes a data/information exchange with the target server over the network. If the target server does not make a response, the mobile network terminal device will increase the connection count by 1, and determine whether the connection count is greater than 3. If the connection count is greater than 3, the user is prompted that the network connection is failed, and the work flow is ended. Preferably, during the pathological image monitoring, the user can also operate the keyboard to issue a sending instruction, so as to make a video data transmission in real time.

Figure 13:
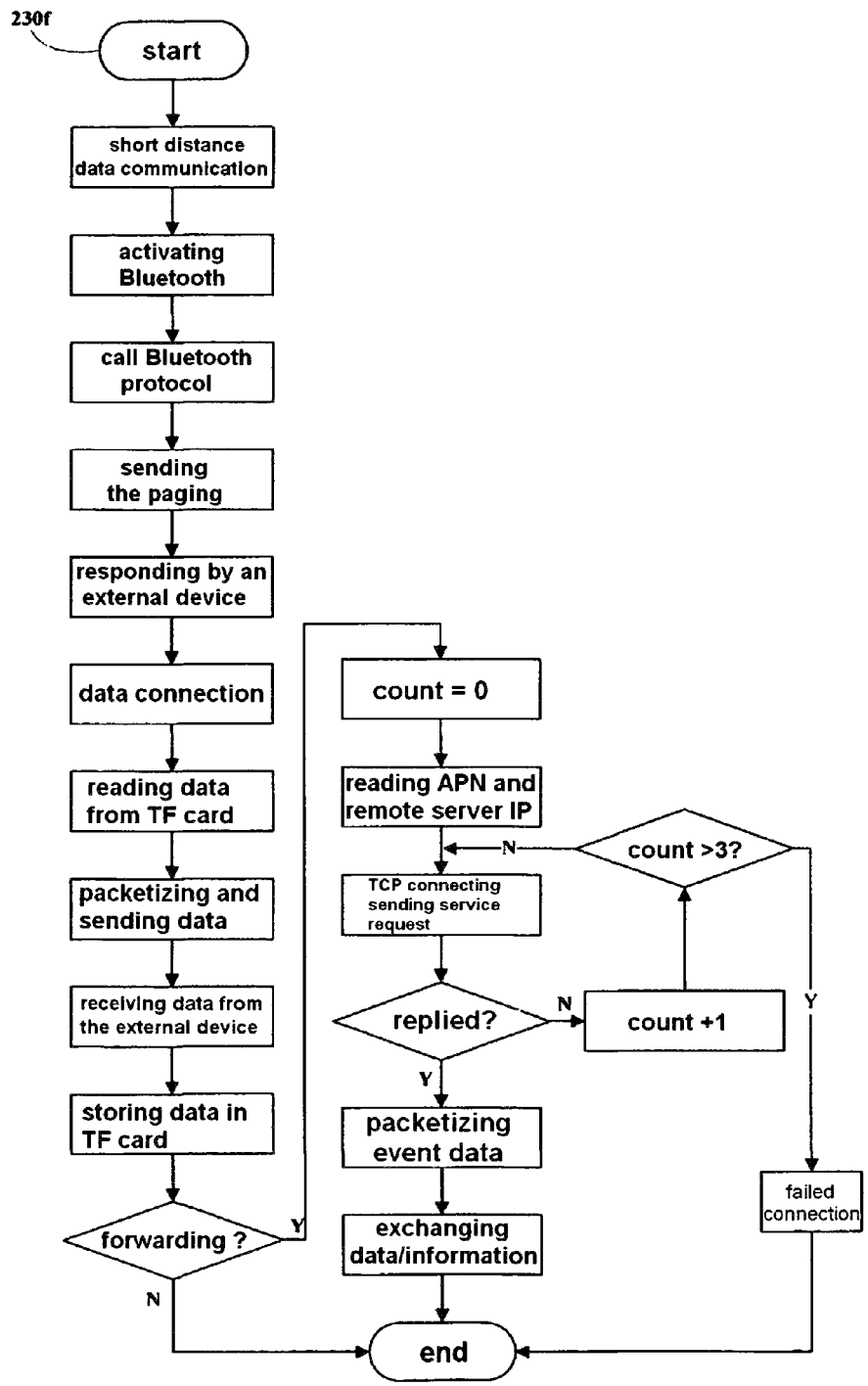
FIG. 13 is a flow chart illustrating the process steps of the mobile network terminal device in the short distance data communication mode.

FIG. 13 is a flow chart illustrating the process steps of the mobile network terminal device in the short distance data communication mode. The mobile network terminal device proceeds into the short distance data communication work status 230f. According to the work mode flag, the mobile network terminal device activates the Bluetooth module 108 and calls the Bluetooth protocol, drives the Bluetooth module 108 to send a paging signal to the external device. The Bluetooth of the external device makes a response. According to the response flag DAC (device access code) replied from the Bluetooth of the external device, the Bluetooth module 108 sends a FH synchronization packet, exchanges the real time clock and the flag information, and establishes a data channel connection. Under the control of the application program module 200, the mobile network terminal device reads the data stored in the external data storage card 106, packetizes the data, and makes the short distance data/information exchange. The mobile network terminal device can be connected to an external Bluetooth printer through the Bluetooth module 108, so as to print a monitoring chart report. In the case where the mobile network is lacked or can not be used, the mobile network terminal device can be connected to a local area network and a broadband network with a Bluetooth interface, so as to transmit data over the network. In addition, the mobile network terminal device can also exchange the data/information with a Bluetooth digital cell phone, and a Bluetooth smart device.

The Bluetooth module 108 of the mobile network terminal device receives the data/information including the medical data from the external device, and then sends the received data/information to and stores the received data/information in preset area of the external data storage card 106. When the forwarding of external data is required, according to the forwarding instruction sent from the user keyboard, the mobile network terminal device reads the access point domain name APN and the target server IP address stored in the external data memory 107, sets the previous network connection count to be zero at the same time, registers with the GPRS mobile network, establishes the data connection to the target server, sends the local host user flag and the service category request flag. According to the response flag replied from the target server, the mobile network terminal device reads the data to be forwarded from the external data storage card 106, packetizes the data, and forwards the data of the external device to the target server. If the target server does not make a response, the mobile network terminal device will increase the connection count by 1, and determine whether the connection count is greater than 3. If the connection count is greater than 3, the user is prompted that the network connection is failed, and the work flow of this forwarding of the data is ended.

In accordance with one embodiment of the present invention, depending on the work mode flag, data packetized by the mobile network terminal device as mentioned in FIGS. 8-13 can be the electrophysiological data, the local host user medical record summary, the society medical insurance card number, and the position information data which are packetized together; can also be the pathological image video data, the local host user medical record summary, the society medical insurance card number, and the position information data which are packetized together; and can also be the forwarded external data. The electrophysiological data can be current event data, and can also be electrophysiological monitoring summary data in several days and several weeks. The electrophysiological monitoring summary data mainly summarizes the featured electrophysiological abnormal data occurred in a certain time period, for example, premature ventricular contractions, cardiac arrest, paroxysmal tachycardia, transient ST segment change, systolic blood pressure SBP higher than 140 mmHg, diastolic blood pressure DBP higher than 90 mmHg, sleep apnea time length, and so on, or makes a summary review on the electrophysiological data in a normal range for a certain time period.

Figure 14:
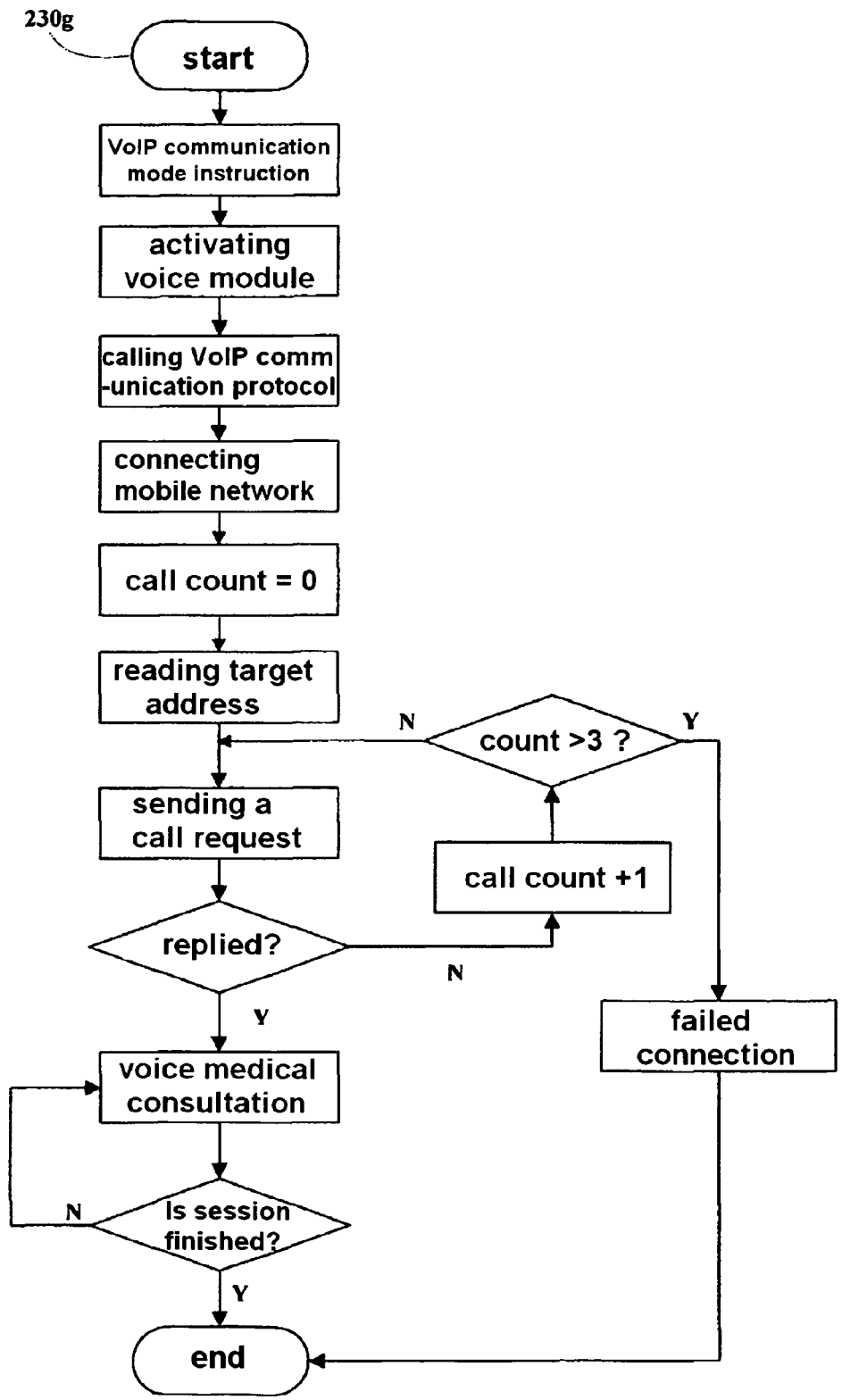
FIG. 14 is a flow chart illustrating the process steps of the mobile network terminal device in the VoIP voice communication mode.

FIG. 14 is a flow chart illustrating the process steps of the mobile network terminal device in the VoIP voice communication mode. The mobile network terminal device proceeds into the VoIP voice communication work mode 230g. According to the work mode flag, the mobile network terminal device activates the voice module 105, calls the VoIP communication protocol, makes the mobile network connection, and sets a previous call count to be zero at the same time. Then, the mobile network terminal device reads the VoIP access information and the default target address stored in the external data memory 107, and launches a call request. If the target end responds to the request successfully, the callee at the target end will perform the step of the voice medical consultation. If the target end does not respond to the request successfully, a call count is increased by 1, and whether the call count is greater than 3 is determined. If the call count is greater than 3, the user is prompted that the call fails, and the whole flow is ended. Otherwise, it returns to the step of launching a call request. During the voice medical consultation, it is determined whether a session is finished. If the session is finished, the whole flow is ended; otherwise, it returns to the step of making the voice medical consultation. Preferably, the default target address can be set to be a target hospital electrophysiological remote guardianship center solely, and also can be set to be a plurality of target addresses including the addresses of the relatives of the user, and the call request is launched for the plurality of the target addresses circularly.

Figure 15:
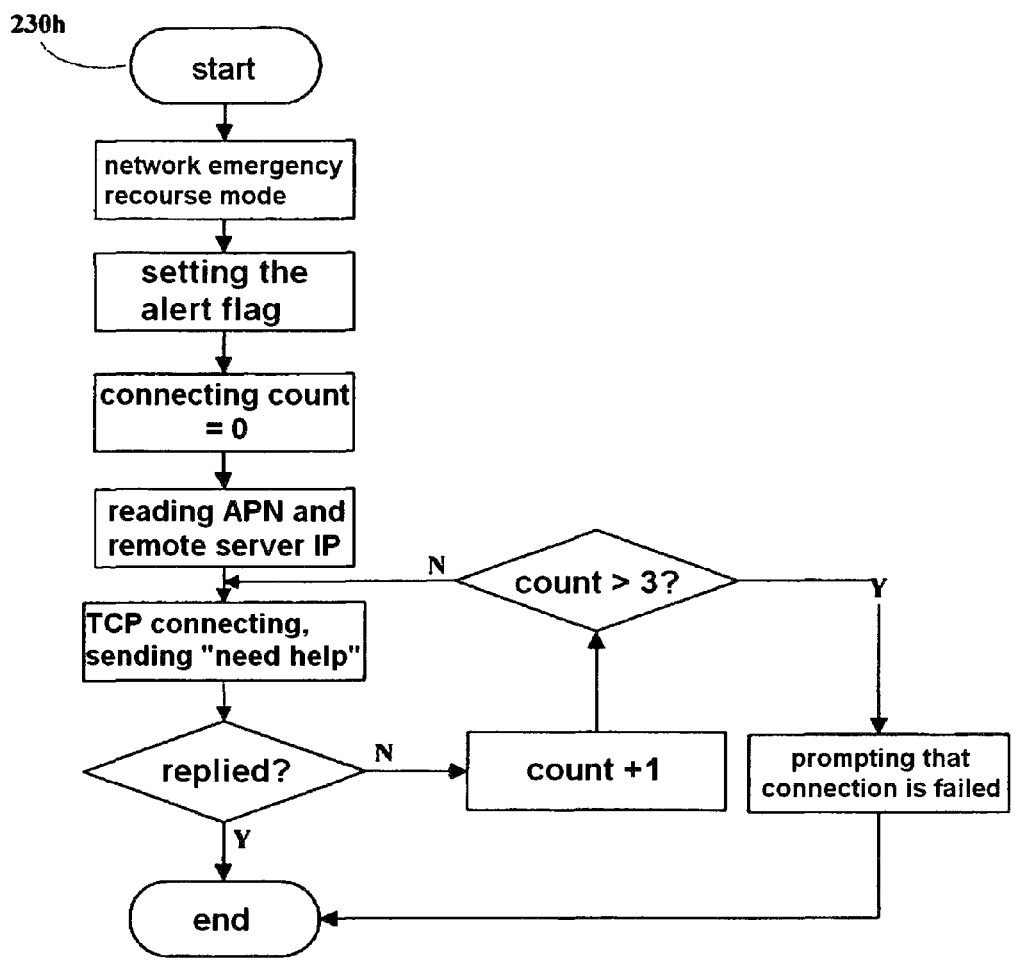
FIG. 15 is a flow chart illustrating the process steps of the mobile network terminal device in the network emergency recourse mode.

FIG. 15 is a flow chart illustrating the process steps of the mobile network terminal device in the network emergency recourse mode. When the user triggers the emergency recourse key to send instructions, the mobile network terminal device proceeds into the network emergency recourse work status 230h. According to the work mode recognition flag, the mobile network terminal device sets the alarm category flag; sends the audio alert and/or the vibration alert, the light alert; and sets the previous network connection count to be zero at the same time. Then the mobile network terminal device reads the access point domain name APN and the target server IP address stored in the external data memory 107, registers with the GPRS mobile network, establishes the data connection to the target server, and sends the local host user flag, a request flag "I need help", and position information/data to the target server. If the target server makes a response, the mobile network terminal device will end this network emergency recourse work according to the response. The user waits for the rescue provided by the doctors or other persons at the target end. If the target server does not respond to the request, the connection count is increased by 1, and whether the connection count is greater than 3 is determined. If the connection count is less than 3, it returns to the step of launching the network emergency recourse request. If the connection count is greater than 3, the user is prompted that the network connection is failed and other emergency recourse measures should be taken. Accordingly, this network emergency recourse work flow is ended. Preferably, the target server address of the network emergency recourse can be set to be the address of the electrophysiological remote guardianship centre of the hospital solely, and can also be set to be a plurality of addresses involving the emergency system such as 120 and 911 etc. of the district where the user is located, and the cell phone MMS of the user's relatives. The emergency recourse request can be sent to the plurality of addresses simultaneously.

In accordance with one embodiment of the present invention, the Nucleus operation system in the GPRS baseband processor module 100 is embedded with a multimedia software. When the function selection is set to be in the multimedia function status, a multimedia function list is displayed on the screen by the graphic and image display module 103. When selecting a electronic text, the user can open and read eBooks such as the medical materials, a pharmacy manual and so on. When selecting a game, the user can play the intelligence recovery game by operating the keyboard. When selecting a video, the user can play the installed video clips such as cardiac pulmonary resuscitation etc., and an operation flow animation video of the mobile network terminal device. In addition, an audio can also be played at the same time, for the convenience of the aged people.

In accordance with one embodiment of the present invention, a WAP browser is embedded in the Nucleus operation system, and the user can register with the portal websites by using the WAP browser.

In accordance with one embodiment of the present invention, the GPRS baseband processor module 100 has a short message function (SMS), so as to receive and send medical text information; and further has a multimedia message function (MMS), so as to receive and send a medical video, picture, sound, and text information simultaneously.

The electrophysiological data monitoring function of the present invention has a good extension; can be used to the cardiogram data remote mobile monitoring through multiple channels; and can also be used to simultaneously access a cardiogram sensor, a blood pressure sensor, a breath sensor, so as to synchronously make the cardiogram, blood pressure, and breath data remote mobile monitoring.

The application program module and the electrophysiological data collection module 101 of the present invention can be integrated and embedded into the baseband processor module, such that this baseband processor module becomes the baseband processor module dedicated for the remote medical data processing.

The present invention employs an object-oriented programming language (Preferably, C++ language) to write the application program, which has a good extensibility and transplantability, and is suitable for the usage of various standard baseband processors.

Although the specific embodiments of the present invention have been described above, those skilled in this art will understand those specific embodiments are only illustrative explanations. Without departing from the principle and the essential of the present invention, various omissions, replacements and modifications can be made to the details of the above method and device by those skilled in this art. For example, it falls into the scope of the present invention that some steps of the above method are combined, such that substantially same functions are performed in accordance with the substantially same method, so as to achieve substantially same results. Therefore, the scope of the present invention is merely defined by the claims.

The invention claimed is:

1. A mobile network terminal device for monitoring electrophysiological data and a pathological image, characterized in that, the device comprises:
    a baseband processor module, in which an operation system and an application program module which operates in the operation system are embedded, the baseband processor module is used for an electrophysiological data analog to digital conversion of said mobile network terminal device and a processing of various data, and is used for connecting with a mobile network so as to make a data/information exchange over the mobile network;
    an electrophysiological data collection module for collecting electrophysiology analog signal data;
    a keyboard module for sending various control instructions;
    a graphic and image display module for displaying a human machine interaction interface of said mobile network terminal device;
    an image and picture sensor, by which said mobile network terminal device obtains user image and picture video data;
    a voice communication module for VoIP voice communication of said mobile network terminal device;
    an external data storage card for storing various electrophysiology monitoring data of said mobile network terminal device, pathological image video data, external forwarding data, position information data, and multimedia data;
    an external data memory for storing the application program module of said mobile network terminal device, a user information file and a configuration file, and user setting information data, two dimensional code recognition data, and medical evidence data;
    a Bluetooth module for establishing a short distance data/information exchange channel between said mobile network terminal device and an external device;
    a USB interface module for connecting said mobile network terminal device to the external device so as to make a large volume data/information exchange; and
    a GPS receiver module for a satellite positioning of said mobile network terminal device;
    under the control of said application program module, said mobile network terminal device
        selects and/or sets a function status, a work mode, and an analog to digital conversion sampling frequency;
        makes an electrophysiological data remote mobile monitoring, an electrophysiological data remote mobile monitoring in special occasions, a heart pacemaker remote mobile monitoring, a reservation remote consultation, a pathological image remote mobile monitoring, a Bluetooth short distance data/information exchange, a USB large volume data/information exchange, medical consultation VoIP voice communication, and a emergency recourse over the network; and
        views a medical material electronic text, plays an intelligence recovery game, and plays a video in a multimedia work status;
    by means of the application program module, said mobile network terminal device sets an interrupt frequency of a timer unit GPTn of the baseband processor module to be an integer power of 2, sets an interrupt callback function to be a sampling function or a frequency-division sampling function, so as to control and set a sampling frequency or a frequency-division sampling frequency for the analog to digital conversion in each channel of the multiple analog to digital (AD) convertor; and the sampling frequency or the frequency-division sampling frequency ranges from 128 Hz to 16,384 Hz.

2. The mobile network terminal device for monitoring electrophysiological data and a pathological image according to claim 1, characterized in that,
said electrophysiological data collection module comprises at least a plurality of analog signal channels;
output ends of the analog signal channels are respectively connected to input ends of a multiple analog to digital (AD) convertor unit of the baseband processor module;
input ends of the analog signal channels are connected to a multiple cardiogram sensor, so as to synchronously collect multiple cardiogram analog signal data; or
the input ends of the analog signal channels are simultaneously connected to a cardiogram sensor, a blood pressure sensor, and a breath sensor, so as to synchronously collect the cardiogram, the blood pressure, and the breath analog signal data.

3. The mobile network terminal device for monitoring electrophysiological data and a pathological image according to claim 1, characterized in that, the operation system of said mobile network terminal device is embedded with at least a TCP/IP protocol, a Bluetooth protocol, a USB protocol, a WAP browser, an instant message protocol, a VoIP protocol, a multimedia software, and a general language text font; and the operation system is one of general embedded operation systems.

4. The mobile network terminal device for monitoring electrophysiological data and a pathological image according to claim 1, characterized in that, the work mode of said mobile network terminal device includes an electrophysiological data monitoring mode, an electrophysiological data special monitoring mode, a heart pacemaker monitoring mode, a reservation remote consultation mode, a pathological image monitoring mode, a short distance data communication mode, a USB data communication mode, a VoIP voice communication mode, and a network emergency recourse mode.

5. The mobile network terminal device for monitoring electrophysiological data and a pathological image according to claim 1, characterized in that, said keyboard module is connected to a keyboard control unit interface of the baseband processor module, such that said mobile network terminal device inputs user control instruction and user information data, and selects and/or sets the function status and the work mode.

6. The mobile network terminal device for monitoring electrophysiological data and a pathological image according to claim 5, characterized in that, the user information data comprises an access point domain name APN, a target server fixed IP address, a user name and password, a SMS number, a MMS address, VoIP access information, a default target address list, a user identity, a dwelling place, a blood type, a society medical guarantee card number, a medial record summary, text information, and the user information file and the configuration file stored in the external data memory by category.

7. The mobile network terminal device for monitoring electrophysiological data and a pathological image according to claim 1, characterized in that, said graphic and image display module is connected to a graphic and image display control unit interface of the baseband processor module, so as to display the human machine interaction interface of said mobile network terminal device, a function selection list, a work mode selection list, data, an image, a graphic, a text, a letter, and a medical material electronic text page and a video picture in the multimedia work status.

8. The mobile network terminal device for monitoring electrophysiological data and a pathological image according to claim 1, characterized in that, said image and picture sensor is connected to an image/picture collecting and processing unit interface of the baseband processor module, such that said mobile network terminal device obtains the pathological image and picture video data of the user.

9. The mobile network terminal device for electrophysiological data remote monitoring according to claim 1, characterized in that, input ends of a speaker, an earpiece, and a microphone in said a voice communication module are connected to an audio processing unit interface of the baseband processor module respectively, such that the mobile network terminal device makes medical consultation VoIP voice communication over the mobile network, voice broadcasts doctor advice on diagnosis process, a doctor leave word, a user preset medical log content, and an alarm alert which are replied from the target server, and plays an audio in the multimedia work status.

10. The mobile network terminal device for monitoring electrophysiological data and a pathological image according to claim 1, characterized in that, said external data storage card is connected to an external data storage card control unit interface of the baseband processor module, so as to be encoded and divided into a continuous electrophysiological data storage area, an abnormal electrophysiological data storage area, a pathological image video data storage area, an external forwarding data storage area, a position information data storage area, and a multimedia data storage area, and store various data of said mobile network terminal device by category.

11. The mobile network terminal device for monitoring electrophysiological data and a pathological image according to claim 1, characterized in that, said external data memory is connected to an external data memory control unit interface of the baseband processor module, such that said mobile network terminal device stores the application program module, the user information file and the configuration file, the user information data, the two dimensional code recognition data, and the medical evidence data.

12. The mobile network terminal device for monitoring electrophysiological data and a pathological image according to claim 1, characterized in that, said Bluetooth module is connected to a UART1 interface in an asynchronous series communication port UART unit of the baseband processor module, such that said mobile network terminal device makes a short distance data/information exchange with the external device,
said external device includes at least a Bluetooth printer, a Bluetooth digital cell phone, a Bluetooth smart device, and a local area network and a broadband network with a Bluetooth interface.

13. The mobile network terminal device for monitoring electrophysiological data and a pathological image according to claim 1, characterized in that, said USB interface module is connected to a USB controller unit interface of the baseband processor module, such that said mobile network terminal device is connected with an USB interface of the external device to make a large volume data/information exchange, download 24 hours continuous electrophysiological monitoring data from said mobile network terminal device, or receive the medical material electronic text, the intelligence recovery game, and an video clip from the external device.

14. The mobile network terminal device for monitoring electrophysiological data and a pathological image according to claim 1, characterized in that, said GPS receiver module is connected to a UART2 interface in the asynchronous series communication port UART unit of the baseband processor module, such that the mobile network terminal device makes a satellite positioning to obtain information on the position where the user locates, sends the user position information to and stores it in a preset area of the external data storage card, and provides a remote server with the user position information while exchanging data over the network.

15. The mobile network terminal device for monitoring electrophysiological data and a pathological image according to claim 1, characterized in that, the baseband processor module of said mobile network terminal device includes the GPRS, CDMA, and 3G baseband processor modules.

16. A method for monitoring electrophysiological data and a pathological image, comprising: operating an application program module in an operation system of a baseband processor module, controlling a mobile network terminal device to select and/or set a work mode, said work mode includes an electrophysiological data monitoring mode, an electrophysiological data special monitoring mode, a heart pacemaker monitoring mode, a reservation remote consultation mode, a pathological image monitoring mode, a short distance data communication mode, voice communication VoIP mode, and a network emergency recourse mode, characterized in that, further comprising the steps of:

[1] the work mode of the mobile network terminal device is selected and/or set according to instructions generated from operating a keyboard by a user, and a work mode recognition flag is sent;

[2] when the electrophysiological data monitoring mode is selected in step [1], according to the work mode recognition flag, the mobile network terminal device sets an interrupt frequency of a timer unit GPTn of the baseband processor module to be an integer power of 2, sets an interrupt callback function to be a sampling function, and sets a sampling frequency to be at least 128 Hz by the application program module;

[3] the mobile network terminal device reads an access point domain name APN and a target server IP address simultaneously, registers with the mobile network, establishes a data connection to the target server, and sends a local host user flag and a service category request flag;

[4] according to a response flag replied from the target server, the mobile network terminal device controls a microprocessor unit (MCU) of the baseband processor module to enter a sleep state, and keeps an online network connection by the application program module;

[5] data of each channel of a multiple analog to digital (AD) convertor unit of the baseband processor module is read by the sampling function according to the preset sampling frequency, and the electrophysiological data is sent to and stored in a buffer memory unit of the baseband processor module;

[6] a record storage flag is regularly sent by the sampling function, and the microprocessor unit (MCU) of the baseband processor module performs a storage command, reads data from the buffer memory unit, and then sends the data to and stores the data in a preset area of a external data storage card;

[7] the electrophysiological data is analyzed by the application program module, if the electrophysiological data exceeds an alert threshold, an alarm category flag will be set, and an audio alert and/or a vibration alert, a light alert, and a text alert will be sent;

[8] according to the alarm category flag, the mobile network terminal device reads event data stored in the external data memory card, packetizes the data, and makes a data/information exchange over the network under the control of the application program module;

[9] the target server sends a command online, and the mobile network terminal device performs instructions of the target server according to the target server command flag.

17. The method for monitoring electrophysiological data and a pathological image according to claim 16, further comprising:

[10] when the electrophysiological data special monitoring mode is selected in step [1], according to the work mode recognition flag, the mobile network terminal device turns off power supplies of a voice module and a radio frequency antenna unit of the baseband processor module under the control of the application program module;

[11] the mobile network terminal device sets the interrupt frequency of the timer unit GPTn of the baseband processor module to be an integer power of 2, sets the interrupt callback function to be the sampling function, and sets the sampling frequency to be at least 128 Hz;

[12] data of each channel of the multiple analog to digital (AD) convertor unit of the baseband processor module is read by the sampling function according to the preset sampling frequency, and the electrophysiological data is sent to and stored in the buffer memory unit;

[13] the record storage flag is regularly sent by the sampling function, and the microprocessor unit (MCU) of the baseband processor module performs the storage command, reads data from the buffer memory unit, and then sends the data to and stores the data in a preset area of the external data storage card;

[14] the electrophysiological data is analyzed by the application program module, if the electrophysiological data exceeds the alert threshold, the alarm category flag will be set, the vibration alert and/or the light alert, and the text alert will be sent so as to prompt the user to launch a network data communication function by operating the keyboard;

[15] according to instructions from the user keyboard, the mobile network terminal device activates the radio frequency antenna unit of the baseband processor module, reads the access point domain name APN and the target server IP address, registers with the mobile network, establishes the data connection to the target server, and sends the local host user flag and the service category request flag;

[16] according to the response flag replied from the target server, the mobile network terminal device reads event data stored in the external data memory card, packetizes the data, and makes a data/information exchange over the network under the control of the application program module.

18. The method for monitoring electrophysiological data and a pathological image according to claim 16, further comprising:

[17] when the heart pacemaker monitoring mode is selected in step [1], according to the work mode recognition flag, the mobile network terminal device turns off the power supply of the radio frequency antenna unit of the baseband processor module under the control of the application program module;

[18] the mobile network terminal device raises the interrupt frequency of the timer unit GPTn of the baseband processor module, sets the interrupt frequency to be the integer power of 2, sets the interrupt callback function to be a frequency-division sampling function, sets the sampling frequency of the pacemaker pulse channel to be at least 2,048 Hz;

[19] data of each channel of the multiple analog to digital (AD) convertor unit of the baseband processor module is read by the frequency-division sampling function according to the preset frequency-division sampling frequency, the pacemaker pulse data is compressed, and then sent to and stored in the buffer memory unit;

[20] the record storage flag is regularly sent by the frequency-division sampling function, and the microprocessor unit (MCU) of the baseband processor module performs the storage command, reads data from the buffer memory unit, and then sends the data to and stores the data in a preset area of the external data storage card;

[21] the pacemaker pulse data is analyzed by the application program module, if the pacemaker pulse data exceeds the alert threshold, the alarm category flag will be set, the audio alert and/or the vibration alert, the light alert, and the text alert will be sent so as to prompt the user to launch a network data communication function by operating the keyboard;

[22] according to instructions from the user keyboard, the mobile network terminal device activates the radio frequency antenna unit of the baseband processor module, reads the access point domain name APN and the target server IP address, registers with the mobile network, establishes the data connection to the target server, and sends the local host user flag and the service category request flag;

[23] according to the response flag replied from the target server, the mobile network terminal device reads event data stored in the external data memory card, packetizes the data, and makes a data/information exchange over the network under the control of the application program module.

19. The method for monitoring electrophysiological data and a pathological image according to claim 16, further comprising:

[24] when the reservation remote consultation mode is selected in step [1], according to the work mode recognition flag, the mobile network terminal device sets wake up time T of a real time clock unit of the baseband processor module;

[25] when the preset time T of the real time clock unit elapses, an activation signal flag will be sent;

[26] according to the activation signal flag, the mobile network terminal device reads the access point domain name APN and the target server IP address, registers with the mobile network, establishes the data connection to the target server, and sends the local host user flag and the service category request flag;

[27] according to the response flag replied from the target server, the mobile network terminal device reads data stored in the external data memory card, packetizes the data, and makes a data/information exchange over the network under the control of the application program module.

20. The method for monitoring electrophysiological data and a pathological image according to claim 16, further comprising:

[28] when the pathological image monitoring mode is selected in step [1], according to the work mode recognition flag, the mobile network terminal device sets a pathological image monitoring time length T, and activates an image and picture sensor;

[29] the image and picture sensor focuses automatically, takes pathological image video data of the user, and then sends the data to and stores the data in a preset area of the external data storage card;

[30] when the pathological image monitoring preset time T elapses, the mobile network terminal device goes into a wait-to-send status;

[31] according to sending instructions issued from the user keyboard, the mobile network terminal device reads the access point domain name APN and the target server IP address, registers with the mobile network, establishes the data connection to the target server, and sends the local host user flag and the service category request flag;

[32] according to the response flag replied from the target server, the mobile network terminal device reads video data stored in the external data memory card, compresses a data packet, and makes a data/information exchange over the network under the control of the application program module.

21. The method for monitoring electrophysiological data and a pathological image according to claim 16, further comprising:

[33] when the short distance data communication mode is selected in step [1], according to the work mode recognition flag, the mobile network terminal device activates a Bluetooth module to send a paging signal to an external device;

[34] according to a Bluetooth response flag "device access code (DAC)" of the external device, the Bluetooth module of the mobile network terminal device sends a FH synchronization packet, exchanges real time clock and flag information, and establishes a data channel connection;

[35] the mobile network terminal device reads data stored in the external data memory card under the control of the application program module, and makes a short distance data/information exchange;

[36] the Bluetooth module of the mobile network terminal device receives the data/information sent from the external device, sends the data/information to and stores the data/information in a preset area of the external data storage card under the control of the application program module;

[37] according to forwarding instructions issued from the user keyboard, the mobile network terminal device reads the access point domain name APN and the target server IP address, registers with the mobile network, establishes the data connection to the target server, and sends the local host user flag and the service category request flag;

[38] according to the response flag replied from the target server, the mobile network terminal device reads data stored in the external data memory card, packetizes the data, and forwards the data of the external device under the control of the application program module.

22. The method for monitoring electrophysiological data and a pathological image according to claim 16, further comprising:

[39] when the VoIP voice communication mode is selected in step [1], according to the work mode recognition flag, the mobile network terminal device activates a voice module, and registers with the mobile network simultaneously;

[40] the mobile network terminal device calls a VoIP voice communication protocol by the application program module, reads VoIP access information and a default target address stored in the external data memory, and initiates a request for establishing a call;

[41] a callee at the target end makes a response to the request, and the mobile network terminal device and the callee at the target end make voice medical consultation or voice communication.

23. The method for monitoring electrophysiological data and a pathological image according to claim 16, further comprising:

[42] when the network emergency recourse mode is selected in step [1], according to the work mode recognition flag, the mobile network terminal device sets the alarm category flag by the application program module, and sends the audio alert and/or the vibration alert and the light alert;

[43] the mobile network terminal device reads the access point domain name APN and the target server IP address stored in the external data memory, registers with the mobile network, establishes the data connection to the target server, and circularly sends the local host user flag, a request flag "I need help", and position information data;

[44] according to the response flag replied from the target server, the mobile network terminal device quits the network emergency recourse work mode.

24. The method for monitoring electrophysiological data and a pathological image according to claim 16, characterized in that, said mobile network terminal device receives the command and date sent online by the target server, the command and date are standard or customized, and include at least a function setting command, a device internal data/information obtaining command, a service category response command, and an abnormal event alarm command.

25. The method for monitoring electrophysiological data and a pathological image according to claim 16, characterized in that, the data packetized by said mobile network terminal device can be electrophysiological data, a local host user medical record summary, a society medical insurance card number, and position information data which are packetized together; can also be pathological image video data, a local host user medical record summary, a society medical insurance card number, and position information data which are packetized together; and can also be forwarded external data; the packetized electrophysiological data can be current event data, and can also be electrophysiological monitoring summary data in several days and several weeks.

* * * * *